United States Patent
Blondel et al.

(10) Patent No.: US 10,561,597 B2
(45) Date of Patent: *Feb. 18, 2020

(54) USE IN COSMETICS OF POLYMERS OBTAINED BY LOW-CONCENTRATION, INVERSE EMULSION POLYMERISATION WITH A LOW LEVEL OF NEUTRALISED MONOMERS

(71) Applicant: S.P.C.M. SA, Andrezieux Boutheon (FR)

(72) Inventors: Frederic Blondel, Lezigneux (FR); Lionel Champagnon, Magneux Haute Rive (FR)

(73) Assignee: S.P.C.M. SA, Andrezieux Boutheon (FR)

( * ) Notice: Subject to any disclaimer, the term of this patent is extended or adjusted under 35 U.S.C. 154(b) by 215 days.

This patent is subject to a terminal disclaimer.

(21) Appl. No.: 15/025,392

(22) PCT Filed: Oct. 7, 2014

(86) PCT No.: PCT/FR2014/052536
§ 371 (c)(1),
(2) Date: Mar. 28, 2016

(87) PCT Pub. No.: WO2015/052426
PCT Pub. Date: Apr. 16, 2015

(65) Prior Publication Data
US 2016/0228348 A1 Aug. 11, 2016

(30) Foreign Application Priority Data

Oct. 7, 2013 (FR) .................................. 13 59693

(51) Int. Cl.
| | | |
|---|---|---|
| A61K 8/06 | (2006.01) | |
| A61K 8/81 | (2006.01) | |
| C08F 120/06 | (2006.01) | |
| C08F 220/06 | (2006.01) | |
| A61Q 5/00 | (2006.01) | |
| A61Q 5/02 | (2006.01) | |
| A61Q 19/00 | (2006.01) | |
| A61Q 19/10 | (2006.01) | |

(52) U.S. Cl.
CPC .............. *A61K 8/8147* (2013.01); *A61K 8/06* (2013.01); *A61K 8/062* (2013.01); *A61K 8/064* (2013.01); *A61Q 5/00* (2013.01); *A61Q 5/02* (2013.01); *A61Q 19/00* (2013.01); *A61Q 19/10* (2013.01); *C08F 120/06* (2013.01); *C08F 220/06* (2013.01); *A61K 2800/48* (2013.01)

(58) Field of Classification Search
None
See application file for complete search history.

(56) References Cited

U.S. PATENT DOCUMENTS

| | | | |
|---|---|---|---|
| 2,438,091 A | 3/1948 | Lynch | |
| 2,528,378 A | 10/1950 | Mannheimer | |
| 2,658,072 A | 11/1953 | Kosmin | |
| 3,284,393 A | 11/1966 | Vanderhoff et al. | |
| 3,724,547 A | 4/1973 | Bott | |
| 3,755,560 A | 8/1973 | Dickert et al. | |
| 4,421,769 A | 12/1983 | Dixon et al. | |
| 4,539,368 A | 9/1985 | Duncan et al. | |
| 4,656,222 A * | 4/1987 | DeFazio | C08F 20/06 524/762 |
| 4,677,152 A | 6/1987 | Allen et al. | |
| 4,704,272 A | 11/1987 | Oh et al. | |
| 4,741,855 A | 5/1988 | Grote et al. | |
| 4,788,006 A | 11/1988 | Bolich, Jr. et al. | |
| 5,004,598 A | 4/1991 | Lochhead et al. | |
| 5,011,681 A | 4/1991 | Ciotti et al. | |
| 5,216,070 A * | 6/1993 | Plochocka | C08F 2/32 524/109 |
| 5,368,850 A | 11/1994 | Cauwet et al. | |
| 5,380,465 A | 1/1995 | Baker et al. | |
| 5,484,843 A | 1/1996 | Mallo et al. | |
| 5,679,656 A | 10/1997 | Hansenne | |
| 5,928,656 A | 7/1999 | Chaudhry et al. | |
| 6,024,946 A | 2/2000 | Dubief et al. | |

(Continued)

FOREIGN PATENT DOCUMENTS

| | | |
|---|---|---|
| DE | 19523596 | 1/1997 |
| EP | 0 161 038 | 11/1985 |

(Continued)

OTHER PUBLICATIONS

B Kriwet, E Walter, T Kissel. "Synthesis of bioadhesive poly(acrylic acid) nano- and microparticles using an inverse emulsion polymerization method for the entrapment of hydrophilic drug candidates." Journal of Controlled Release, vol. 56, 1998, pp. 149-158. (Year: 1998).*

(Continued)

*Primary Examiner* — Isaac Shomer
(74) *Attorney, Agent, or Firm* — Heslin Rothenberg Farley & Mesiti P.C.

(57) ABSTRACT

A cosmetic or dermatological composition comprising at least one aqueous phase, of a branched or crosslinked polymer is obtained by polymerization of an aqueous solution of one or more monomers in water-in-oil inverse emulsion, at least one of the monomers used being an acrylic monomer and one or more of the monomers used being a monomer bearing at least one weak acid function, the molar percentage of monomers bearing at least one weak acid function relative to all of the monomers used being at least 30 mol %. The polymerization is carried out with a concentration of all the monomers in aqueous solution lying in the range 1.3 mmol to 3.6 mmol per gram of aqueous solution. During the polymerization, at most 20% of the acid functions present on the monomers having at least one acid function are in neutralized form. The compositions are intended for treatment of keratinous materials.

30 Claims, No Drawings

(56) References Cited

U.S. PATENT DOCUMENTS

| | | | |
|---|---|---|---|
| 6,197,287 B1 | 3/2001 | Mallo et al. | |
| 9,290,588 B2 * | 3/2016 | Blondel | C08F 2/32 |
| 9,963,532 B2 * | 5/2018 | Blondel | C08F 220/06 |
| 2003/0147825 A1 * | 8/2003 | Chiarelli | A61K 8/06 424/70.11 |
| 2004/0028637 A1 | 2/2004 | Villard et al. | |
| 2007/0036741 A1 * | 2/2007 | Villard | B01F 17/0071 424/70.16 |
| 2007/0265386 A1 | 11/2007 | Mallo et al. | |
| 2014/0309368 A1 | 10/2014 | Blondel et al. | |

FOREIGN PATENT DOCUMENTS

| | | |
|---|---|---|
| EP | 0 503 853 | 9/1992 |
| EP | 0 576 188 | 12/1993 |
| EP | 0 604 249 | 6/1994 |
| FR | 2 979 821 | 3/2013 |
| WO | 92/21318 | 12/1992 |
| WO | 93/07902 | 4/1993 |
| WO | 94/27561 | 12/1994 |
| WO | 98/09611 | 3/1998 |
| WO | 2005/097834 | 10/2005 |

OTHER PUBLICATIONS

Jian Fang GE et al., "Investigation on the...of Acrylic Acid", Chinese Chemical Letters, vol. 13, No. 10, pp. 993-996, 2002.

* cited by examiner

USE IN COSMETICS OF POLYMERS OBTAINED BY LOW-CONCENTRATION, INVERSE EMULSION POLYMERISATION WITH A LOW LEVEL OF NEUTRALISED MONOMERS

The invention relates to the technical field of cosmetic or dermatological compositions and, more precisely, to the use in said field of synthetic acrylic polymers comprising at least one weak acid function, obtained in particular conditions by the inverse emulsion polymerization process from at least one monomer bearing a weak acid function, as well as the corresponding cosmetic compositions.

The cosmetic or dermatological compositions generally include an aqueous phase. They are applied in particular on the skin or hair, and they are generally in the form of oil-in-water emulsions, and sometimes water-in-oil emulsions, for example in order to form creams or lotions. Such compositions may, for example, correspond to anti-ageing creams or lotions, after-shave skincare, moisturizing creams, hair coloring lotions, shampoos, conditioners, conditioning shampoos, shower products, cleansing creams, or also ointments or sun creams or lotions. Creams differ from lotions by their greater viscosity.

Rheology modifiers or thickeners are widely used in said compositions in order to adapt their sensory profile (appearance, application) to consumer demand, and also in order to suspend or stabilize active principles.

In order to do so, various types of thickener/viscosifier have already been proposed:

Natural and/or modified gums, such as guar, hydroxyethyl cellulose, or also of biopolymers such as xanthan, are used. Said polymers, which are non ionic to slightly anionic, are not very sensitive to the charged species often present in the compositions (ethylene-diamene-tetracetic acid (EDTA), ionic active principles . . . ), but intrinsically they have little effect and they are known for obtaining textures that are not very attractive and that tend, during application, to procure a sticky/tacky sensation and to leave a film after drying.

Synthetic products of the carbomer, crosslinked acrylic acid homopolymer type obtained by precipitation polymerization are also used. Nevertheless, the method used obtaining them results in the presence of residual organic solvents of the benzene, chlorinated solvent, or indeed cyclohexane type that present toxicological profiles that are not satisfactory for cosmetic application. Furthermore, those polymers require a neutralizing step during preparation by the formulator in order to be able to develop thickening properties. That type of polymer may present good suspending capacities but remains ineffective for emulsifying the oil phase. For that reason, U.S. Pat. No. 5,004,598, in the name of The BF Goodrich Company, proposes an acrylic acid-based copolymer with a small amount of a hydrophobic monomer, thus obtaining properties that are emulsifying, but not very viscosifying.

The use of pre-neutralized powders and liquid dispersions in organic oils of (co)acrylic polymers, obtained by inverse emulsion polymerization has also been proposed. Said polymers have much better ability for emulsifying oil phases, but they also remain less effective than a carbomer and they lead to problems of residues during application. Patent application WO 2005/097834 in the name of CIBA proposes improving viscosifying properties (effectiveness) by neutralizing monomers bearing an acid function prior to polymerization, with a degree of neutralization lying in the range 25% to 100%, and more preferably lying in the range 30% to 40%.

Patents EP 0 503 853 and EP 1 047 716 propose 2-acrylamido-2-methylpropane sulfonic acid (ATBS)-based inverse emulsion polymers making it possible to viscosity cosmetic or dermatological compositions including with an acid pH. Even if those polymers, and those described in application WO 2005/097834, have made it possible to improve thickening effectiveness in compositions of that type, they still do not satisfy user requirements. Such users are seeking new solutions that are more effective, i.e. proposing better thickening effectiveness possibly with less polymer, while allowing a wider range of formulations with ionic compounds. Furthermore, polymers containing a large quantity of ATBS are expensive, and another challenge is to propose polymers at a lower cost.

It has been observed that due to their highly anionic character, the resistance of the majority of said polymers to electrolytes is generally low. Because of that, they are highly sensitive to electrolytes. However, cosmetic or dermatological compositions contain electrolytes.

Electrolytes are positively or negatively-charged chemical substances and are capable of transporting or conducting an electric charge, generally in a solution. They are also referred to as "ionic compounds" and in the field of cosmetic and dermatological composition formulation, as "ionic ingredients". They may be monovalent or multivalent. Electrolytes are primarily acids, bases, or salts. More precisely, from among electrolytes often found in cosmetic and dermatological compositions, mention may be made of additives such as vegetable extracts containing monovalent or divalent ions, active principles such as hydroxy acids for their anti-ageing effect, moisturizing agents such as pyrrolidone carboxylic acid (PCA), chelating agents such as for example ethylenediaminetetraacetic acid (EDTA), UV filters such as phenylbenzimidazole sulfonic acid, certain preservatives, or also salts such as for example alum salt. The electrolytes present in the compositions therefore have an effect on the effectiveness of the thickeners resulting in a high reduction in the viscosity of the composition. It then is necessary to increase the quantity of thickening polymers in order to obtain satisfactory thickening of the composition.

Furthermore, the epidermis on which the creams, shampoos, or lotions are applied also contains electrolytes such as for example sodium chloride. Application of a cream or lotion that is not sufficiently resistant to electrolytes will then give a disagreeable sensation of liquefaction on contact with the skin.

In order to overcome that problem, patent application US 2003/0147825 in the name of NOVEON proposes using a polymer in the form of an inverse emulsion comprising an amphiphilic acrylic monomer. Nevertheless, said polymers lead to cream textures that are quite structured, even gelled, that do not correspond to the expectations of the consumer. It should be noted that about 60% to 100%, or about 75% to 95% of the monomers containing carboxylic acid groups are neutralized before the polymerization reaction (see paragraph [0042]), which corresponds to conventionally-implemented conditions. Specifically, it is mentioned in various documents relating to acrylic polymer preparation directly carried out via a water-in-oil inverse emulsion polymerization process (in particular as described in document U.S. Pat. No. 5,216,070), that, for feasibility reasons, it is necessary, when the desired polymers are prepared from at least one monomer comprising a weak acid function, such as acrylic acid, to use, for carrying out the polymerization reaction, monomers of which the weak acid function is in neutralized form, in order to avoid precipitation problems during the use of a process of preparation via inverse emulsion. U.S. Pat. Nos. 5,380,465, 4,539,368, and 4,656,222, and the publication from Chinese Chemical Letters Vol. 13, No 10, pp 993 to 996, 2002, for example, all use high-percentage neutralization, or even total neutralization, of monomers bearing a weak acid function for carrying out the inverse emulsion polymerization reaction. As indicated in particular in U.S. Pat. No. 5,216,070, the preparation of such polymers in the absence of neutralization of the monomers bearing a weak acid function that are used, directly via the inverse emulsion polymerization process, poses a precipitation/destabilization problem.

There therefore seems to exist a real need for improving existing cosmetic and dermatological compositions. The object being to propose compositions of attractive appearance and satisfactory stability, that are adapted to having any type of (mono or multivalent) ionic ingredients incorporated therein, and that therefore present excellent resistance to electrolytes. In this context, one of the objects of the applicant has been to develop polymers that are obtained by inverse emulsion polymerization and that exhibit improved thickening performance levels, but above all that present better resistance to the electrolytes conventionally used in cosmetic and dermatological compositions.

In order to thicken cosmetic or dermatological compositions, the invention thus proposes the use of an acrylic polymer obtained by implementing particular conditions in an inverse emulsion polymerization process, said polymer having improved resistance to electrolytes, while conserving good thickening effectiveness and while giving an attractive appearance to the compositions.

For producing a cosmetic or dermatological composition comprising at least one aqueous phase, the present invention provides the use of a branched or crosslinked polymer composed of the repetition of one or more monomeric units, with at least one of the monomeric units corresponding to a monomer comprising an acrylic group, and at least 30 molar percent (mol %) of the monomeric units bearing at least one weak acid function, possibly in neutralized form, said polymer being obtained:

by polymerization of an aqueous solution of one or more monomers in water-in-oil inverse emulsion, at least one of the monomers used being an acrylic monomer and one or more of the monomers used being a monomer bearing at least one weak acid function, the molar percentage of monomers bearing at least one weak acid function relative to all of the monomers used being at least 30%, the aqueous phase containing at least one monomer acting as branching agent, in such a manner that polymerization leads to a branched or crosslinked polymer, characterized in that:

i) the polymerization is carried out with a concentration of all the monomers in aqueous solution lying in the range 1.3 millimoles (mmol) to 3.6 mmol per gram of aqueous solution; and ii) during the polymerization, at most 20% of the acid functions present on the monomers having at least one acid function are in neutralized form;

the polymerization possibly being followed by one or more of the following steps:

diluting or concentrating the resulting emulsion;
isolating to obtain the polymer in the form of a powder; and
at least partially neutralizing free acid functions present in the resulting polymer.

Such a polymer defined by the process for obtaining it is referred to in the description below as a "thickening polymer", "acrylic polymer", or "branched or crosslinked polymer".

The invention also provides the use of such a thickening polymer, to thicken, or even thicken and emulsify, a cosmetic or dermatological composition comprising at least one aqueous phase. In preferred manner, in order to obtain the desired thickening effect, the thickening polymer includes a percentage of neutralized acid functions in the range 30% to 100% relative to all of the acid functions present on the polymer, which percentage is obtained by a step of at least partial neutralization of the acid functions present on the polymer and carried out after the polymerization, but before or after preparing the composition.

The invention further provides cosmetic or dermatological compositions comprising at least one aqueous phase and a such thickening polymer, the polymerization being followed by a step of at least partial neutralization of the acid functions present, carried out before or after incorporating the polymer in the composition; and possibly by one or more of the following steps, carried out before incorporating the polymer in the composition:

diluting or concentrating the resulting emulsion; and
isolating to obtain the polymer in the form of a powder.

The use of a composition of the invention for cosmetic or dermatological treatment of keratinous material such as the skin, the scalp, the eyelashes, the eyebrows, the nails, hair and/or mucous membranes, excluding any therapeutic treatment, is also an integral part of the invention. Such use includes application of the composition to keratinous material, possibly followed by rinsing with water.

The uses and compositions of the present invention preferably present one or more of the characteristics described below, or any combination of said characteristics, or even all of the characteristics given below when they are not mutually exclusive:

during the polymerization, at most 10%, preferably at most 5%, and more preferably at most 2%, of the acid functions present on the monomers having at least one acid function are in neutralized form; According to one particular embodiment, all of the acid functions present on the monomers used are in free acid form during the polymerization;

the polymerization is carried out with a concentration of all the monomers in aqueous solution lying in the range 1.7 mmol to 3.3 mmol per gram of aqueous solution;

the polymer includes a molar percentage of monomeric units bearing one or more weak acid function(s), relative to all of the monomeric units bearing an acid function, of at least 50%, preferably of at least 70%, more preferably of at least 80%;

all the monomers used for preparing the polymer are monomers possessing at least one ethylenically unsaturated bond;

the monomeric unit(s) bearing at least one weak acid function, in free form, is/are chosen from acrylic acid, methacrylic acid, itaconic acid, crotonic acid, maleic acid, and fumaric acid, acrylic acid being preferred;

the polymer is a copolymer including at least one neutral monomeric unit chosen from acrylamide, methacrylamide, N,N-dimethylacrylamide, N-vinylmethylacetamide, N-vinylformamide, vinyl acetate, diacetone acrylamide, N-isopropylacrylamide, N-[2-hydroxy-1,1-bis(hydroxymethyl)ethyl]propenamide, (2-hydroxyethyl) acrylate, (2,3-dihydroxypropyl) acrylate, methyl methacrylate, (2-hydroxyethyl) methacrylate, (2,3-dihydroxypropyl) methacrylate, and vinylpyrrolidone;

either all of the monomeric units bearing at least one acid function present in the polymer are monomeric units bearing one or more weak acid function(s). In particular, the polymer present in the composition is an acryl/acrylamide acid copolymer with lying in the range 30% to 100% acrylic acid functions in neutralized form; or else the polymer is a copolymer including at least one monomeric unit bearing one or more strong acid function(s). In preferred manner, the molar percentage in monomeric units bearing one or more strong acid function(s) relative to all of the monomeric units is less than 50%, and preferably less than 30%. By way of example, the monomeric unit(s) bearing one or more strong acid function(s), in free form, is/are chosen from acrylamidoalkylsulfonic acids such as 2-acrylamido-2-methylpropane sulfonic acid. In particular, the polymer present in the composition is a copolymer of 2-acrylamido-2-methylpropane sulfonic acid and acrylic acid, or of 2-acrylamido-2-methylpropane sulfonic acid and acrylic acid and acrylamide, with 30% to 100% acid functions present on the polymer that are in neutralized form;

the branching agent is chosen from methylenebisacrylamide (MBA), ethylene glycol diacrylate, polyethylene glycol dimethacrylate, diacrylamide, cyanomethyl acrylate, vinyloxyethyl acrylate, vinyloxy methacrylate, triallylamine, formaldehyde, glyoxal, glycidyl ethers such as ethylene glycol diglycidyl ether, and epoxies, and mixtures thereof;

the amount of branching agent is between 5 ppm and 10000 ppm by weight, relative to the total weight of monomer, and preferably between 100 ppm and 5000 ppm;

the polymerization reaction is carried out in the presence of a water-in-oil emulsifier;

the polymerization is carried out with a transfer agent, e.g. chosen from methanol, isopropyl alcohol, sodium hypophosphite, 2-mercaptoethanol, and sodium methallyl sulfonate, and mixtures thereof; preferably, the amount of transfer agent is between 0 ppm and 5000 ppm by weight, relative to the total weight of monomer, and preferably between 10 ppm and 2500 ppm;

when the branched or crosslinked polymer used in the composition is at 0.16% by weight in demineralized water at pH that was adjusted to 7±0.1 with sodium hydroxide, it presents viscosity as measured at 25° C. with a Brookfield viscometer of the RVT type (rotation speed 20 revolutions per minute (rpm), that lies in the range 2000 milliPascal seconds (mPa·s) to 100000 mPa·s, in particular in the range 3000 mPa·s to 50000 mPa·s. The procedure for measuring the viscosity of the aqueous solution of polymer at 0.16% by weight is as follows. 250 grams (g) of deionized water are placed in a 400 milliliter (mL) beaker and then, with mechanical stirring (three-blades—500 rpm), the desired amount of inverse emulsion is gradually added so as to obtain a solution containing 0.160% by weight of active polymer. Preferably, the added polymer is in the form (inverse emulsion, dry powder, solution in water . . . ) in which it is used for preparing the cosmetic or dermatological composition. The pH is then adjusted to 7±0.1 with sodium hydroxide. At this pH, 100% of the acid functions present on the polymer are neutralized. The solution is stirred for 15 minutes and then left to stand for 5 minutes. The viscosity is then measured by means of a Brookfield viscometer of the RVT type (rotation speed 20 rpm). The branched or crosslinked polymer present in the composition thus serves to thicken the composition to a certain viscosity, measured at 25° C. with the Brookfield equipment, that lies in the range 100 mPa·s to 100.000 mPa·s, in particular in the range 100 mPa·s to 50.000 mPa·s. In particular, the emulsions, lotions, and creams of the invention are of viscosity lying in the range 1000 mPa·s to 50 000 mPa·s, preferably in the range 5000 mPa·s to 40 000 mPa·s. Shampoos, conditioners, and shower products of the invention are of viscosity lying in the range 100 mPa·s to 10 000 mPa·s, preferably in the range 300 mPa·s to 5000 mPa·s;

the composition is suitable for topical application. By way of example, the composition is in the form of a milk, a lotion, a gel, a cream, a gel cream, a soap, a bubble bath, a balm, a shampoo or conditioner, or a shower product;

the composition comprises an electrolyte, preferably selected from among vegetable extracts containing monovalent or divalent ions such as fruit acids, active principles such as hydroxy acids for their anti-ageing effect, moisturizing agents such as pyrrolidone carboxylic acid, chelating agents such as ethylenediaminetetraacetic acid (EDTA), ultraviolet (UV) filters such as phenylbenzimidazole sulfonic acid, certain preservatives, or also salts such as alum salts;

the composition comprises in the range 0.01% to 10% by weight of branched or crosslinked polymer, relative to the total weight of the composition, and preferably in the range 0.1% to 5% by weight of branched or crosslinked polymer;

the composition comprises at least one active agent chosen from moisturizing agents, tanning agents, sunscreens, vitamins, oligo-elements, anti-wrinkle or anti-ageing agents, botanical extracts, slimming agents, anti-radical agents, anti hair-loss agents, anti-dandruff agents, skin-conditioning polymers, cleansing surfactants, emollients and pharmaceutical active principles such as anti-fungal agents, anti-bacterial agents, anti-inflammatory agents, myorelaxants, antibiotics, antiviral agents, analgesics, anti-histamines, antipruritic agents, antipyretic agents, anesthetic agents, diagnostic agents, hormones, skin growth enhancers, pigment modulators, antiproliferative agents, antipsoriatic agents, retinoids, anti-acne drugs, antineoplastic agents, phototherapeutic agents, keratolytic agents, and analogs thereof;

the composition comprises at least one additive, and in particular at least one formulation aid, for example chosen from chelating agents, thinners, pH neutralization and adjustment agents, opacifiers, preservatives, leveling agents, emollients, film-forming polymers, antioxidants, perfumes, reflective agents, coalescing agents, and mixtures thereof;

the composition is an emulsion of an oily phase in an aqueous phase or an emulsion of an aqueous phase in an oily phase;

the oily phase is made up of a vegetable or plant oil, a silicone oil, a fluorinated hydrocarbon oil, a hydrocarbon oil, a mineral oil, polyisobutene, isohexadecane, a caprylic/capric triglyceride, cetearyl octanoate, $C_{12}$-$C_{14}$ alkyl benzoate, or a mixture thereof; and the composition comprises a water-in-oil emulsifier and/or an oil-in-water emulsifier.

The thickening polymers used in the context of the invention and the process for obtaining them are described first.

The polymers used in the context of the invention are made up of repeats of one or more monomeric units, with at least one of the monomeric units corresponding to a monomer comprising an acrylic group. In other words, they correspond to homopolymers obtained by polymerizing a monomer comprising an acrylic group or to copolymers obtained by copolymerizing a mixture of monomers, at least one of which comprises an acrylic group. For simplification purposes, in the description below, such polymers may be referred to more simply as acrylic polymers.

In order to ensure they are effective in acting as a thickener, the polymers used in the context of the invention are water-soluble or water-swelling and they are therefore found in the aqueous phase of the composition. The monomers used for preparing said polymers and in particular the level of hydrophilic monomers are selected so as to obtain such properties.

The term "water-soluble polymer" is used to mean a polymer which, when put into solution in water by stirring at a temperature of 25° C. and at a concentration of 50 grams per liter (g/L), gives a solution free of insoluble particles.

The term "water-swelling polymer" is used to mean a polymer which, when put into solution in water at a temperature of 25° C., swells and thickens the solution.

The polymers used in the context of the invention are branched or crosslinked. The term "branched polymer" is used in conventional manner to mean nonlinear polymers which have side chains. Branched polymers include in particular polymers in star form or in comb form. The term "crosslinked polymer" is intended to mean, conventionally, a nonlinear polymer which is in the form of a three-dimensional network that is water-insoluble, but water-swellable.

Crosslinking is obtained by using a branching agent during polymerization, which agent is integrated in the aqueous phase. Such a branching agent corresponds to a monomer comprising two or more ethylenic unsaturations and, by way of example, chosen from methylenebisacrylamide (MBA), ethylene glycol diacrylate, polyethylene glycol dimethacrylate, diacrylamide, cyanomethyl acrylate, vinyloxyethyl acrylate, vinyloxy methacrylate, triallylamine, formaldehyde, glyoxal, glycidyl ethers such as ethylene glycol diglycidyl ether, and epoxies, and mixtures thereof.

It should be specified that, in the context of the invention, the total concentration of monomers given in relation to the polymerization process includes the monomers acting as a branching agent.

In the context of the invention, the applicant has investigated the use of corresponding acrylic polymers or acrylic polymers obtained from an inverse emulsion prepared by water-in-oil inverse emulsion polymerization with use of a high molar percentage of monomers bearing one or more weak acid function(s) relative to all the monomers used, and in particular including at least 30 mol % of monomers bearing at least one weak acid function. With such a level of monomers bearing a weak acid function, the inventors have demonstrated that the properties of the polymer obtained actually depend, firstly, on the degree of neutralization of the acid functions of the monomers used during the polymerization and, secondly, on the total concentration of monomers in the aqueous phase. In a manner that is original compared with the approaches proposed in the prior art which recommend carrying out the polymerization with a high degree of neutralization of the acid functions, the applicant has turned, in the context of the invention, to a process for inverse emulsion polymerization of polymers exhibiting a low degree of neutralization and, in particular, a degree of neutralization of at most 20% for the acid functions that are present.

In the context of the invention, the applicant provides a process for using such a polymer, obtained by polymerizing an aqueous solution of monomers in water-in-oil inverse emulsion, in which the polymerization is carried out with a concentration of all the monomers that lies in the range 1.3 mmol to 3.6 mmol per gram of aqueous solution. Furthermore, the applicant has demonstrated that, contrary to the higher concentrations used in particular in the prior art, such a concentration range is compatible with obtaining a polymer with a low degree of neutralization of the weak acid functions present, and makes it possible to avoid the stability problems observed in the prior art.

In the context of the invention, the polymer used is obtained by implementing a process for preparing a polymer by polymerizing an aqueous solution of one or more monomers in water-in-oil inverse emulsion, in which one or more of the monomers used comprise(s) at least one acid function, the molar percentage of monomers bearing at least one weak acid function relative to all the monomers used being at least 30%, characterized in that:

i) the polymerization is carried out with a concentration of all the monomers in aqueous solution that lies in the range 1.3 mmol to 3.6 mmol per gram of aqueous solution; and ii) during the polymerization, at most 20% of the acid functions present on the monomers used that have at least one acid function are in neutralized form.

In particular, during the polymerization, at most 10%, preferably at most 5%, and more preferably at most 2%, of the acid functions present on the monomers used that have at least one acid function are in neutralized form, thereby making it possible to obtain thickening properties that are even more advantageous. In one particular embodiment, 100% of the acid functions present on the monomers used are in free acid form during the polymerization.

In the context of the invention, optimally, the polymerization is carried out with a total concentration of monomers present in the aqueous solution that lies in the range 1.7 to 3.3 mmol per gram of aqueous solution. In the context of the invention, the monomer concentrations are given relative to the total weight of aqueous solution (also known as aqueous phase), i.e. weight of monomers included.

In particular, it is therefore possible to carry out the polymerization with the following combinations:

a concentration of all the monomers in aqueous solution lying in the range 1.3 mmol to 3.6 mmol per gram of aqueous solution, with at most 20%, advantageously at most 10%, preferably at most 5%, and more preferably at most 2%, or even 0%, of the acid functions present on the monomers having at least one acid function being in neutralized form; and a concentration of all the monomers in aqueous solution that lies in the range of from 1.7 mmol to 3.3 mmol per gram of aqueous solution, with at most 20%, advantageously at most 10%, preferably at most 5%, and more preferably at most 2%, or even 0%, of the acid functions present on the monomers having at least one acid function being in neutralized form.

The molar percentage of monomers bearing at least one weak acid function relative to all the monomers used is preferably at least 50%, more preferably at least 70%, and most preferably at least 80%. Such molar percentages can be used with any of the above-mentioned combinations of monomer concentration and degree of neutralization.

In the context of the invention, the polymerization is preferably be carried out with monomers that all have at least one ethylenic unsaturation.

Preferably, the polymerization is carried out with a single monomer bearing at least one weak acid function, at a molar percentage relative to all the monomers used of at least 30%, which in free form is chosen from acrylic acid, methacrylic acid, itaconic acid, crotonic acid, maleic acid, and fumaric acid. The monomer bearing at least one weak acid function is most preferably acrylic acid in free form or with a degree of neutralization in accordance with the invention. It is also possible to use a plurality of monomers each bearing at least one weak acid function, in particular chosen from those previously listed, and having a total molar percentage of which relative to all the monomers used of at least 30%. Preferably, one of these monomers is acrylic acid in free form or with a degree of neutralization in accordance with the invention.

The polymerization can be carried out with at least one monomer bearing at least one strong acid function. In this case, the polymerization is preferably carried out with monomers bearing at least one strong acid function at a concentration relative to all the monomers used that is less than 50%, and preferably less than 30%. By way of example, the polymerization may be carried out with a monomer bearing at least one strong acid function, which, in free form, is chosen from acrylamidoalkylsulfonic acids, such as 2-acrylamido-2-methylpropanesulfonic acid (ATBS). By way of example, the polymerization can then be carried out with a combination of acrylic acid and ATBS or of acrylic acid and ATBS and acrylamide, the acid monomers possibly being in free form or with a degree of neutralization in accordance with the invention.

In the context of the invention, it has been noted that, by selecting a monomer concentration lying in the range 1.3 mmol to 3.6 mmol per gram of aqueous solution for carrying out the inverse emulsion polymerization reaction, it is possible to prepare inverse emulsions of polymers bearing an acid function with a low degree of neutralization, or even no neutralization, which are stable, i.e. without observing a rapid precipitation phenomenon. Furthermore, it has been demonstrated that contrary to the higher concentrations used in the prior art, such a concentration range combined with weak neutralization of the acid functions present, makes it possible to obtain polymers that provide thickening and/or stabilizing effectiveness, after a step of at least partial neutralization, that is greater than the prior art polymers obtained by inverse emulsion polymerization. In addition, it has been shown that said polymers are more resistant to electrolytes, and that use thereof in the production of cosmetic or dermatological compositions makes it possible to reduce the drop in viscosity due to the presence of electrolytes. Their thickening effectiveness is therefore improved and the compositions obtained present an attractive appearance.

The expression "monomer bearing at least one acid function" is intended to mean a monomer bearing one or more acid function(s) that are free or neutralized (i.e. salified by the action of a base) acid function(s). The term "acid function", without going into more detail is thus used to mean both the acid functions both in free form and in neutralized form. When a monomer comprises more than one acid function, it is possible to have only some of the acid functions in neutralized form. The acid function(s) present may be functions of a weak acid or of a strong acid. In general, the monomers used comprise only weak acid functions or only strong acid functions, and most commonly, monomers bearing a single acid function are used. The same definitions and preferences apply to the monomeric units present on the polymer obtained.

By way of example of a monomer bearing at least one weak acid function in free form, of the —COOH type, mention may be made of acrylic acid, methacrylic acid, itaconic acid, and crotonic acid, which all comprise just one weak acid function, and maleic acid and fumaric acid which, for their part, comprise two weak acid functions.

By way of example of a monomer bearing a strong acid function in free form, mention may be made of monomers bearing a phosphonic acid or sulfonic acid function, for instance acrylamidoalkylsulfonic acids such as 2-acrylamido-2-methylpropanesulfonic acid.

In their neutralized form, the acid functions are in anionic form with a counterion or cation depending on the base used for the neutralization, for example of the Na+ type when sodium hydroxide is used, or else the $NH_4+$ type when aqueous ammonia is used. In conventional manner, the number of acid functions in neutralized form is controlled by the choice of the pH for the aqueous solution of monomers, which should be adjusted according to the acidity content (pKa) of the acid functions present.

The polymerization can involve a single type of monomer, which is then chosen from monomers bearing at least one weak acid function or various monomer types, at least one of which bears at least one weak acid function, with a proportion of the acid functions present on the monomers used, and therefore on the copolymer obtained, in a neutralized form, that is less than or equal to 20%. In particular, in addition to the above-described monomeric units bearing at least one weak acid function, the polymer obtained may contain other monomeric units, such as monomeric units bearing at least one strong acid function, neutral (or nonionic) monomeric units, cationic monomeric units, and/or monomeric units with a hydrophobic nature. Whatever the situation, the conditions for aqueous phase formation and for polymerization are such that the acid functions of the monomers involved remain predominantly in free form, and are not neutralized by formation of a salified form, or weakly neutralized with a degree of neutralization that is limited, being less than or equal to 20%. When neutralization of less than or equal to 20% takes place, it is generally carried out in the aqueous phase, by adding an appropriate amount of base. A base such as sodium hydroxide or aqueous ammonia may be used.

In particular, the polymerization reaction can be carried out with at least one neutral monomer chosen from acrylamide, methacrylamide, N,N-dimethylacrylamide, N-vinylmethylacetamide, N-vinylformamide, vinyl acetate, diacetone acrylamide, N-isopropylacrylamide, N-[2-hydroxy-1,1-bis(hydroxymethyl)ethyl]propenamide, (2-hydroxyethyl) acrylate, (2,3-dihydroxypropyl) acrylate, methyl methacrylate, (2-hydroxyethyl) methacrylate, (2,3-dihydroxypropyl) methacrylate, vinylpyrrolidone, or other acrylic esters, or other ethylenically unsaturated esters. For example, the polymerization can be carried out with lying in the range 30 mol % to 99 mol % of at least one monomer that has one or more weak acid function(s) and lying in the range 1 mol % to 70 mol % of at least one neutral monomer. By way of example, the polymerization may be carried out with an acrylic acid/acrylamide combination, the acrylic acid being in neutral form or having a degree of neutralization in accordance with the invention.

It is also possible to carry out copolymerization with at least one cationic monomer. By way of example, among cationic monomers, mention may be made of diallyldialkylammonium salts, for instance diallyldimethylammonium chloride (DADMAC); acidified or quaternized salts of dialkylaminoalkyl acrylates and methacrylates, in particular of dialkylaminoethyl acrylate (ADAME) and of dialkylaminoethyl methacrylate (MADAME); acidified or quaternized salts of dialkylaminoalkylacrylamides or methacrylamides, for instance methacrylamidopropyltrimethylammonium chloride (MAPTAC), acrylamidopropyltrimethylammonium chloride (APTAC) and Mannich products such as quaternized dialkylaminomethylacrylamides.

The acidified salts are obtained via the means known to those skilled in the art, and in particular by protonation. The quaternized salts are also obtained via the means known to those skilled in the art, in particular by reaction with benzyl chloride, methyl chloride (MeCl), aryl chlorides, alkyl chlorides, or dimethyl sulfate.

It is also possible to carry out copolymerization with at least one monomer of hydrophobic nature. By way of examples of monomers of hydrophobic nature, mention may be made of undecanoic acid acrylamide, undodecyl acid methyl acrylamide, and acrylic acid derivatives such as alkyl acrylates or methacrylates, for instance ethoxylated (25) behenyl methacrylate. Under such circumstances, the molar percentage of monomers of hydrophobic nature relative to all the monomers used is, preferably, less than 10%, and generally between 0.001% and 7%.

In a first variant of the process of the invention, all the monomers bearing at least one acid function that are used to carry out the polymerization are monomers bearing at least one weak acid function.

In a second variant of the process of the invention, the polymerization is carried out with at least one monomer bearing at least one strong acid function, in addition to at least one monomer bearing at least one weak acid function. Under such circumstances, the molar percentage of monomers bearing at least one strong acid function relative to all the monomers used is preferably less than 50%, most preferably less than 30%.

The copolymers obtained by the process of the invention may in particular be made up of a combination of at least one monomeric unit bearing at least one weak acid function and of at least one monomeric unit bearing at least one strong acid function, and may in particular correspond to an copolymer of acrylic acid and ATBS, these acid monomers being in neutral form or having a degree of neutralization in accordance with the invention; made up of a combination of at least one monomeric unit bearing at least one weak acid function with at least one neutral monomeric unit and optionally at least one monomeric unit bearing at least one strong acid function, and in particular may correspond to a copolymer of acrylic acid and acrylamide or to a copolymer of acrylic acid and ATBS/acrylamide, the acrylic acid and the ATBS being in neutral form or having a degree of neutralization in accordance with the invention; may be made up of a combination of at least one monomeric unit bearing at least one weak acid function with at least one cationic monomeric unit and optionally at least one monomeric unit bearing at least one strong acid function; or else may be made up of a combination of at least one monomeric unit bearing at least one weak acid function with at least one neutral monomeric unit and at least one cationic monomer and optionally at least one monomeric unit bearing at least one strong acid function.

In the inverse emulsion polymerization process used in the context of the invention, the monomers are put into an aqueous solution. This aqueous solution corresponds to the aqueous phase of the inverse emulsion. In the context of the invention, in the aqueous solution used for the polymerization, at most 20% of the acid functions present on the monomers having at least one acid function are in neutralized form.

It is also possible to use a transfer agent, otherwise known as a chain limiter. The use of a transfer agent is particularly advantageous for controlling the molecular weight of the resulting polymer. By way of example of a transfer agent, mention may be made of methanol, isopropanol, sodium hypophosphite, 2-mercaptoethanol, and sodium methallyl sulfonate, and mixtures thereof. In known manner, those skilled in the art can adjust the amounts of branching agent, and optionally of transfer agent, that are used according to whether they wish to obtain a branched polymer or a crosslinked polymer.

In greater detail, the process in the context of the invention comprises the following steps:

a) providing an aqueous solution of the selected monomer(s), termed the aqueous phase;

b) emulsifying said aqueous solution in a water-immiscible phase, termed the oil phase; and c) carrying out the polymerization reaction.

Of course, the aqueous solution of step a) has a total concentration of monomers, a molar percentage of monomers bearing at least one weak acid function relative to all the monomers used and a degree of neutralization of the acid functions present on the monomers having at least one acid function, which are in accordance with the process described in the context of the invention.

In conventional manner, step b) of emulsifying the aqueous phase in the oil phase, is preferably done by adding the aqueous phase to the oil phase while stirring.

In general, the polymerization reaction is carried out in the presence of a water-in-oil emulsifier. The latter is most commonly introduced into the oil phase in which the aqueous solution is emulsified. The term "emulsifier of the water-in-oil (W/O) type" is intended to mean an emulsifier which has a hydrophilic lipophilic balance (HLB) value sufficiently low to provide water-in-oil emulsions, and in particular an HLB value of less than 10.

The HLB value is calculated according to the following relationship:

$$HLB = (\% \text{ by weight of the hydrophilic part})/5$$

where the percentage by weight of the hydrophilic part is the ratio of the molecular weight of the hydrophilic part to the total molecular weight of the molecule.

By way of example of such water-in-oil emulsifiers, mention may be made of surfactant polymers such as polyesters having a molecular weight between 1000 and 3000 g/mol, products of condensation between a poly (isobutenyl)succinic acid or the anhydride thereof and a polyethylene glycol, block copolymers having a molecular weight between 2500 and 3500 g/mol, for example those sold under the Hypermer® names, sorbitan extracts, for instance sorbitan monooleate, sorbitan isostearate or sorbitan sesquioleate, certain polyethoxylated sorbitan esters, for instance pentaethoxylated sorbitan monooleate or pentaethoxylated sorbitan isostearate, or else diethoxylated oleocetyl alcohol or tetraethoxylated lauryl acrylate.

In the inverse emulsion polymerization process, the aqueous solution contains the monomer(s) and optionally the branching agent and the transfer agent. It may also contain complexing agents such as ethylenediamine or ethylenediaminetetraacetic acid.

Most commonly, the polymerization reaction of step c) is initiated by introducing a free radical initiator into the emulsion formed in step b). By way of example of a free radical initiator, mention may be made of redox couples, with cumene hydroperoxide or tertiary butylhydroxyperoxide among the oxidizing agents, and persulfates such as sodium metabisulfite and the Mohr salt among the reducing agents. Azo compounds such as 2,2'-atobis(isobutyronitrile) and 2,2'-azobis(2-amidinopropane) hydrochloride can also be used.

Conventionally, the polymerization is generally carried out isothermally, adiabatically or at controlled temperature. That is to say the temperature is kept constant, generally between 10° C. and 50° C. (isotherm), or else the temperature is left to increase naturally (adiabatic) and the reaction then generally begins at a temperature below 10° C. and the final temperature is generally above 50° C., or, finally, the temperature increase is controlled so as to have a temperature curve between the isotherm curve and the adiabatic curve.

At the end of the polymerization reaction, it is possible to introduce one or more oil-in-water emulsifiers, preferably at a temperature below 50° C.

The term "emulsifier of the oil-in-water (O/W) type" is intended to mean an emulsifier which has an HLB value that is sufficiently high to provide oil-in-water emulsions and in particular an HLB value of greater than 10. By way of example of such oil-in-water emulsifiers, mention may be made of ethoxylated sorbitan esters such as sorbitan oleate ethoxylated with 20 equivalents of ethylene oxide (EO 20), sorbitan laurate polyethoxylated with 20 mol of ethylene oxide, castor oil polyethoxylated with 40 mol of ethylene oxide, decaethoxylated oleodecyl alcohol, heptaethoxylated lauryl alcohol, or sorbitan monostearate polyethoxylated with 20 mol of ethylene oxide.

The amounts of emulsifier(s) introduced are such that the resulting inverse emulsion of the polymer obtained will generally contain in the range 1% to 10% by weight, and preferably in the range 2.5% to 9% by weight, of emulsifiers of the water-in-oil (W/O) type and, optionally, in the range 2% to 10% by weight, and preferably in the range 2.5% to 6% by weight, of emulsifiers of the oil-in-water (O/W) type.

In general, the weight ratio of the aqueous phase to the oil phase lies in the range 50/50 to 90/10.

By way of example, the oil phase used in the inverse emulsion polymerization process may be composed of a mineral oil, in particular a commercial mineral oil, containing saturated hydrocarbons of paraffinic, isoparaffinic, cycloparaffinic, or naphthyl type having, at ambient temperature (22° C.), specific gravity between 0.7 and 0.9; of a vegetable oil; of a synthetic oil such as hydrogenated polydecene or hydrogenated polyisobutene; of an ester such as octyl stearate or butyl oleate; of a vegetable oil such as squalane of vegetable origin; or of a mixture of several of these oils.

At the end of the polymerization reaction, it is also possible for the emulsion obtained to be diluted or concentrated. In particular, it is possible to concentrate the resulting emulsion by distillation or else it is possible to dry it completely, in order to obtain a powder. Such concentration or drying should be carried out with or without prior introduction of an emulsifier of the oil-in-water (O/W) type.

The inverse emulsions thus obtained using the process according to the invention can be concentrated, for example by distillation. Inverse emulsions are then obtained with a polymer concentration that may be between 30% and 75% by weight, preferably between 40% and 65% by weight.

The polymers obtained from the inverse emulsions of the invention and subsequently subjected to an isolation step, may be in the form of a powder. By way of example, such an isolation step can be chosen from precipitation, azeotropic distillation, and spray-drying techniques.

Indeed, in the context of the invention, it is possible to concentrate or isolate the polymer in the form of an inverse emulsion obtained directly on exiting the inverse emulsion polymerization process, without loss of the advantageous properties of the polymers obtained. There are in particular numerous processes for obtaining powder from inverse emulsions of polymers, which processes consist in isolating the active material from the other constituents of the emulsion, for instance:

precipitating from a nonsolvent medium, such as acetone, methanol or any other polar solvent in which the polymer is not soluble. Simple filtering then makes it possible to isolate the polymer particle;

azeotropic distilling in the presence of an agglomerating agent and of stabilizing polymer makes it possible to produce agglomerates that are easily isolated by filtering before carrying out the drying of the particle;

spray-drying, which consists in creating a cloud of fine droplets of emulsions in a hot air stream, for a controlled period of time.

The polymers obtained after such steps retain their advantageous properties, in terms of thickening ability and in terms of resistance to electrolytes.

Without an additional neutralizing step, in the polymers obtained at the end of the inverse emulsion polymerization process, at most 20% of the acid functions present are in neutralized form, preferably at most 10%, even more preferably at most 5%, and most preferably at most 2%. This low degree of neutralization of the acid functions present provides the formulator with great flexibility in terms of use, making it possible to adjust the properties of the polymer and therefore the desired thickening effect by adjusting the required degree of neutralization. Such an approach also allows the formulator to select the nature of the neutralizing agent used, compatible with the targeted use.

In order to obtain the desired thickening effect, the polymerizing is most commonly followed by a neutralizing step, otherwise known as a post-neutralizing step, for neutralizing at least some, or even all, of the free acid functions present on the polymer. Where a step of at least partially neutralizing the free acid functions present in the polymer obtained is carried out after the polymerization reaction, it preferably results in a percentage neutralization relative to all the acid functions present on the polymer lying in the range 30% to 100%.

Such a post-neutralizing step may be carried out in various ways:

the post-neutralizing may be carried out on the inverse emulsion obtained at the end of the inverse emulsion polymerization process. This generally applies when it is the manufacturer who neutralizes the polymer in inverse emulsion form;

the post-neutralization may be carried out on an aqueous solution obtained following the inversion of the inverse emulsion in water. This generally applies when it is the formulator who uses the inverse emulsion, or the powder ensuing therefrom, in an aqueous solution, called stock solution, before adding it to the medium that is to be thickened. The formulator is then free to adjust the polymer concentration of the solution, the degree of neutralization, and the nature of the neutralizing agents; and the post-neutralizing may also be carried out on the composition containing the inverse emulsion or the powder ensuing therefrom. In the same way as above, the user is free to adjust the degree of neutralization and the nature of the neutralizing agents.

The neutralizing is carried out by means of a base, in a manner similar to the above-described neutralizing of the monomers, in the context of the polymerization process, the nature and the amounts of which are selected by those skilled in the art.

These polymers as neutralized in this way provide much better thickening and electrolyte-resistance properties, all conditions otherwise being equal, compared with the polymers obtained by inverse emulsion polymerization not complying with the concentration and neutralization conditions of the monomers as defined in the process of the invention. Particularly after neutralization, the polymers provide advantageous properties compared with polymers consisting of the same monomers, but prepared by inverse emulsion polymerization directly at higher degrees of neutralization and/or at a different total concentration of monomers.

Advantageously, the polymers obtained by means of the process of the invention make it possible, after complete neutralization of the free acid functions present, or at least after greater neutralization, to thicken and/or stabilize aqueous media much more effectively.

The cosmetic and dermatological compositions of the invention and their preparation processes, and in particular the method of incorporating the above-described polymers, are described below.

The cosmetic or dermatological compositions are, most particularly for topical application. The term "topical application" is used to refer to external application on keratinous materials, which are in particular the skin, the scalp, the eyelashes, the eyebrows, the nails, hair and/or mucous membranes. Since the composition is for topical application, it comprises a physiologically-acceptable medium, i.e. compatible with keratinous material. A topical composition of the invention, designed for being applied on the skin, hair, or the mucous membranes of humans or animals, may consist in a topical emulsion comprising at least one aqueous phase and at least one oil phase.

The production of cosmetic or dermatological compositions is broadly known by the person skilled in the art. It generally consists in combining an aqueous phase, an oil phase, generally with surfactants, and with other ingredients such as admixtures and additives. In the compositions of the invention, the aqueous phase and the oil phase are emulsified to form a water-in-oil emulsion, or more often an oil-in-water emulsion. The oil phase of the topical emulsion may consist in a mixture of one or more oils.

The above-described thickening acrylic polymer may be added at any step in the production of the cosmetic or dermatological composition. The cosmetic or dermatological composition preferably includes in the range 0.01% to 10% by weight of thickening acrylic polymer, and most preferably in the range 0.1% to 5% by weight, these percentages being given relative to the total weight of the composition.

The neutralizing step leading to a percentage of neutralized acid functions in the range 30% to 100% relative to all the acid functions present on the polymer may be carried out before or after incorporation of the polymer in the composition In addition, the advantageous properties of the polymer obtained by inverse emulsion polymerization in the above-described process conserves its advantageous properties, whether it is in the form of a more or less concentrated inverse emulsion, a powder, or an aqueous solution. Consequently, the thickening acrylic polymer may be introduced into the cosmetic or dermatological composition in the form of an inverse emulsion, a powder, or in soluble form, e.g. in water or in an organic solvent, or also in the form of an aqueous or organic dispersion. In general, a water-soluble polymer is introduced into the composition, obtained either by inversion of an inverse emulsion in water, or by dissolving a powder in water. Whatever the form in which it is introduced into the cosmetic or dermatological composition at its time of use, the polymer should be in the aqueous phase in which it acts as a thickener and stabilizer.

The aqueous phase may contain all the ingredients conventionally used in a cosmetic or dermatological composition and that are generally water-soluble. The cosmetic or dermatological composition preferably contains in the range 10% to 99% aqueous phase by weight, and more preferably more than 20% by weight, and most preferably in the range 30% to 95% by weight, these percentages being given relative to the total weight of the composition.

The oil phase may contain all the ingredients conventionally used in a cosmetic or dermatological composition and that are generally not water-soluble. The cosmetic or dermatological composition preferably contains in the range 1% to 99% oil phase by weight, and more preferably less than 80% by weight, and most preferably in the range 5% to 70% by weight, these percentages being given relative to the total weight of the composition.

In the context of the invention, apart from its use of the thickening acrylic polymer forming the subject matter of the invention, the aqueous phase and the oil phase (also called the oily or fatty phase) correspond to what is conventionally is used in cosmetic and dermatological compositions. In particular, reference may be made to application FR 2 979 821 in the name of L'OREAL, the relevant parts of which are repeated below.

The composition of the invention may thus comprise a phase referred to as the "aqueous phase" made up of water and of hydrophilic compounds. Such a phase may include, in addition to water, at least one hydrophilic organic solvent such as alcohols and in particular monoalcohols, linear or branched $C_1$-$C_6$ monoalcohols, such as ethanol, tert-butanol, n-butanol, isopropanol or n-propanol, and polyols such as glycerin, diglycerin, propylene glycol, sorbitol, pentylene glycol, and polyethylene glycols, or indeed even glycol ethers, in particular $C_2$ ethers, and hydrophilic $C_2$-$C_4$ aldehydes.

The oil phase is made up in particular of liquid fats at ambient temperature (in particular at 25° C.). By way of liquid fats at ambient temperature, often referred to as oils, that are usable in the invention, mention may be made of hydrocarbon oils of animal origin such as perhydrosqualene; vegetable hydrocarbon oils such as liquid triglycerides of fatty acids having 4 to 10 carbon atoms such as triglycerides of heptanoic or octanoic acids, or also oils of sunflower, corn (maize), soya, grapeseed, sesame, apricot, macadamia nut, castor, avocado, triglycerides of caprylic/capric acids, jojoba oil, shea butter; linear or branched hydrocarbons of mineral or synthetic origin such as paraffin oils and derivatives thereof, Vaseline, polydecenes, hydrogenated polyisobutene such as Parleam; synthesized esters and ethers, in particular fatty acids such as for example PurCellin oil, isopropyl myristate, 2-ethylhexyl palmitate, octyl-2-dodecyl stearate, octyl-2-dodecyl erucate, isostearyl isostearate; hydroxyl esters such as isostearyl lactate, octylhydroxystearate, octyldodecyl hydroxystearate, diisostearylmalate, triisocetyl citrate, heptanoates, octanoates, decanoates of fatty alcohols; polyol esters such as dioctanoate propylene glycol, neopentylglycol diheptanoate, diethyleneglycol diisononanoate; and pentaerythritol esters; fatty alcohols having from 12 to 26 carbon atoms such as octyldodecanol, 2-butyloctanol, 2-hexyldecanol, 2-undecylpentadecanol, oleic alcohol; partially hydrocarbonated and/or siliconized fluorinated oils; silicone oils such as polymethylsiloxanes (PDMS) optionally volatile, linear or cyclic, liquid or pasty at ambient temperature such as cyclomethicones, dimethicones, possibly including a phenyl group, such as phenyl trimethicones, phenyltrimethylsiloxydiphenyl siloxanes, diphenylmethyl-dimethyl-trisiloxanes, diphenyl dimethicones, phenyl dimethicones, polymethylphenyl siloxanes; and mixtures thereof. Those oils may be present in an amount of 0.01% to 90%, and better in the range 0.1% to 85% by weight, relative to the total weight of the composition.

Most often, the oily phase is made up predominantly of a vegetable oil, a silicone oil, a fluorinated hydrocarbon oil, hydrocarbon oil, a mineral oil, polyisobutene, isohexadecane, a caprylic/capric triglyceride, cetearyl octanoate, $C_{12}$-$C_{14}$ alkyl benzoate, or a mixture thereof.

The composition of the invention may also comprise one or more organic, physiologically-acceptable solvents, that may be present in an amount of 0.1% to 90%, preferably in the range 0.5% to 85%, more preferably in the range 10% to 80% by weight, relative to the total weight of the composition, and better in the range 30% to 50%. Mention may be made in particular of, apart from the above-mentioned hydrophilic organic solvents, liquid ketones at ambient temperature (in particular at 25° C.) such as methylthylketone, methylisobutylketone, diisobutylketone, isophorone, cyclohexanone, acetone; liquid propylene glycol ethers at ambient temperature such as propylene glycol monomethyl, propylene glycol monomethylether acetate, dipropylene glycol mono-n-butyl ether; short chain esters (having 3 to 8 carbon atoms in total) such as ethyl acetate, methyl acetate, propyl acetate, n-butyl acetate, isopentyl acetate; liquid ethers at ambient temperature (in particular at 25° C.) such as diethylether, dimethylether or dichlorodiethylether; liquid alkanes at ambient temperature (in particular at 25° C.) such as decane, heptane, dodecane, isododecane, cyclohexane; aromatic cyclic compounds that are liquid at ambient temperature (in particular at 25° C.) such as toluene and xylene; aldehydes that are liquid at ambient temperature (in particular at 25° C.) such as benzaldehyde, acetaldehyde, and mixtures thereof.

The composition may also advantageously comprise at least one surfactant that is generally present in a quantity between 0.01% and 50% by weight, relative to the total weight of the composition, preferably between 0.1% and 40% by weight, and even more preferably between 0.5% and 30% by weight. That surfactant may be chosen from surfactants that are anionic, amphoteric, non-ionic, cationic, or mixtures thereof. In particular, the composition comprises a water-in-oil emulsifier and/or an oil-in-water emulsifier, preferably chosen from those mentioned above in the context of the polymerization process of the thickening acrylic polymer.

In conventional manner, the compositions of the invention comprise:

at least one active agent chosen from moisturizing agents, tanning agents, sunscreens, emollients, pharmaceutical active principles, vitamins, oligo-elements, anti-wrinkle or anti-ageing agents, skin conditioning polymers, botanical extracts, slimming agents, anti-acne agents, anti-radical agents, anti hair-loss agents, anti-dandruff agents, and cleansing surfactants;

and/or at least one additive, and in particular at least one formulation aid, for example chosen from chelating agents, pH neutralization and adjustment agents, opacifiers, preservatives, leveling agents, emollients, film-forming polymers, antioxidants, perfumes, reflective agents, coalescing agents, and mixtures thereof.

Such active agents and additives are well known to the formulator of cosmetic compositions. In particular, reference could be made to US application 2003/0147825, the relevant parts of which are repeated below.

Moisturizing Agents

Moisturizing agents may be defined as being materials that absorb or release water vapor, as a function of the relative humidity of the environment (Harry's Cosmetology, Chemical Publishing Company Inc., 1982, page 266). As an example of a moisturizing agent, mention may be made of allantoin; pyrrolidonecarboxylic acid and salts thereof; hyaluronic acid and salts thereof; sorbic acid and salts thereof; urea, lysine, arginine, cysteine, guanidine, and of other amino acids; polyhydroxy alcohols such as glycerine, propyleneglycol, hexyleneglycol, hexanetriol, ethoxydiglycol, dimethiconecopolyol, and sorbitol, as well as esters thereof; polyethyleneglycol; glycolic acid and glycolate salts (for example of ammonium and of quaternary alkyl ammonium); chitosan; aloe-vera extracts; seaweed extracts; honey and extracts thereof; inositol; lactic acid and lactate salts (for example ammonium and quaternary alkyl ammonium salts); sugars and starches; sugar and starch derivatives (for example alkoxylated glucose); D-panthenol; magnesium ascorbylphosphate; kojic acid; lactamide monoethanolamine; acetamide monoethanolamine; and analogs thereof, and mixtures thereof. When they are used, moisturizing agents typically constitute in the range 1% to 10% by weight, relative to the total weight of the composition, preferably in the range 2% to 8% by weight, and more preferably, in the range 3% to 5% by weight, relative to the total weight of the composition.

Emollients

An emollient may be defined as being a substance that regulates the speed and amount of water take-up by the skin (Handbook of Cosmetic Science and Technology, Elsevier Science Publishing, 1993, page 175). As an example of an emollient that may be incorporated in the composition of the invention, mention may be made of mineral oils, stearic acid; fatty alcohols such as cetyl alcohol, cetearyl alcohol, myristic alcohol, behenyl alcohol and lauryl alcohol; cetyl acetate in acetylated lanolin alcohol; isostearyl isostearate; guerbert esters; guerbert alcohols; octyl stearate; isostearyl benzoate; dicaprylyl maleate; caprylic or capric triglyceride; Vaseline; lanolin and derivatives thereof; coconut oil; shea butter; ethoxylated beeswax; beeswax and esters thereof; silicone ester ethoxylates; fatty alcohol ester ethoxylates such as ceteareth-20, oleth-5, and ceteth-5; avocado oil or glycerides; sesame oil or glycerides; carthame oil or glycerides; sunflower oil or glycerides; oils of botanical seeds; palm bark oil and glycerides; almond oil and glycerides; volatile silicone oils; non-volatile emollients such as esters of fatty acids and of fatty alcohols, highly branched hydrocarbons, and the like; and analogs thereof; and mixtures thereof. Esters of fatty acids and fatty alcohols include decyl oleate, butyl stearate, myristyl myristate, octyldodecyl stearoyl stearate, hydroxyoctyl stearate, di-isopropyl adipate, isopropyl myristate, ethylhexyl palmitate, isodecyl isopentanoate, $C_{12}$-$C_{15}$ alcohol benzoate, diethylhexyl maleate, PPG-147 butyl ether and PPG-2 myristyl ether propionate, cetearyl octanoate, and analogs thereof, and mixtures thereof. Suitable highly-branched hydrocarbons include isohexadecane, and analogs thereof, hydrogenated polyisobutene, polyisobutene, and mixtures thereof. Volatile silicones, such as cyclic or linear polydimethylsiloxanes, and analogs thereof, are also included. The number of silicon atoms in the cyclic silicones may be in the range 3 to 7 or 4 to 5. "Volatile" means that the silicone has a vapor pressure that is measurable. A description of a volatile silicone may be found in Told and Byers, "Volatile Silicone Fluids for Cosmetics", Cosmetics and Toiletries, volume 91, January 1976, pages 27 to 32. Other suitable emollients include polydimethylsiloxane gums, aminosilicones, phenylsilicones, polydimethylsiloxane, polydiethylsiloxane, polymethylphenylsiloxane, polydimethylsiloxane gums, polymethylphenylsiloxane gums, amodimethicone, trimethylsilylamodimethicone, diphenyldimethylpolysiloxane gums, and analogs thereof. When one or more are present in the composition, it/they represent(s) in the range 1% to 20% by weight, relative to the total weight of the composition, preferably, in the range 2% to 15% by weight, and more preferably in the range 3% to 10% by weight, relative to the total weight of the composition.

Pharmaceutical Active Principles

The pharmaceutical active principle(s) that may be incorporated in the composition of the invention may be any substance, chemical matter, or compound that gives rise to a desired local or systemic pharmaceutical effect. These active principles include, but are not limited to, anti-fungal agents, anti-bacterial agents, anti-inflammatory agents, myorelaxants, antibiotics, antiviral agents, analgesics (for example ibuprofen, acetylsalicylic acid, naproxen, and analogs thereof), anti-histamines, antipruritic agents, antipyretic agents, anesthetic agents, diagnostic agents, hormones, skin growth enhancers, pigment modulators, antiproliferative agents, antipsoriatic agents, retinoids, anti-acne drugs (for example benzoyl peroxide, sulfur, and analogs thereof), antineoplastic agents, phototherapeutic agents, keratolytic agents (for example resorcinol, salicylic acid and analogs thereof), and analogs thereof. When the composition comprises one or more pharmaceutical active principles, they typically represent in the range 0.1% to 20% by weight, relative to the total weight of the composition.

Botanical Extracts

Botanical extracts are defined as being extracts from plants or vegetables that may be obtained by means of various preparations, in particular: a tincture, a liquid extract, a solid extract, a powdered extract, a homeopathic dilution, an extract of an essence, an aqueous extract, and analogs thereof. The properties of said preparations are described in Botanicals: A Phytocosmetic Desk Reference, Franck S. D'Amelio, Sr., CRC Press LLC, 1999, page 39. The botanical extracts include, but are not limited to, extracts of the following plants or vegetables: aloe-vera, alfalfa, apple, artichoke, avena, barberry, bearberry, bee pollen, lingonberry, black walnut, borage, calendula, pimiento, chamomile, bulblets, cucumber, coriander, ginseng, ginger, ginkgo, gotu kola, green tea, henna, honey, chestnut, jasmine flowers, hemp, sweet flag, liquorice root, marigold, oats, orange blossom, papaya, blackberry, periwinkle, rose, rosehip, rosemary, sandalwood, seagrass, spirulina, tea tree oil, walnut, couch grass, white elm, yohimbehe, and analogs thereof. When they are used in compositions of the invention the botanical extract(s) typically represent in the range 0.05% to 2% by weight, relative to the total weight of the composition.

Sunscreens

When sunscreens are incorporated in compositions of invention they are used in safe and effective amounts in terms of photoprotection, i.e. in amounts sufficient to provide photoprotection when the composition is applied, but not so high as to lead to side effects such as skin reactions. Examples of sunscreens include those presented in Segarin et al., Cosmetics Science and Technology, chapter VIII, pages 1890 et seq., as well as in 64 Fed. Reg. 27666 to 27693 (May 21, 1999). As examples of sunscreens, mention may be made of p-aminobenzoic acid, salts thereof and derivatives thereof (ethyl, isobutyl, glyceryl-esters; p-dimethylaminobenzoic acid; 2-ethylhexyl N,N-dimethylaminobenzoate); anthranilates (namely o-aminobenzoates; methyl, octyl, amyl, menthyl, phenyl, benzyl, phenylethyl, linalyl, terpinyl, and cyclohexenyl esters); salicylates (octyl, amyl, phenyl, benzyl, menthyl, glyceryl, and dipropyleneglycol esters); derivatives of cinnamic acid (ethylhexyl-p-methoxy, menthyl and benzyl esters; phenylcinnamonitrile; butyl cinnamoyl pyruvate); derivatives of dihydroxycinnamic acid (umbelliferone, methylumbelliferone, methylaceto-umbelliferone); derivatives of trihydroxycinnamic acid (esculetin, methylsculetin, daphnetin and glycosides, esculin and daphnin); hydrocarbons (diphenylbutadiene, stilbene); dibenzalacetone and benzalacetophenone; naphtosulfonates (sodium salts of 2-napthol-3,6-disulfonic and 2-naphtol-6, 8-disulfonic acids); dihydroxynaphtoic acid and salts thereof; o- and p-hydroxybiphenyldisulfonates; derivatives of coumarin (7-hydroxy, 7-methyl and 3-phenyl); diazoles (2-acethyl-3-bromoindazole, phenylbenzoxacole, methylnaphtoxazole, and various arylbenzothiazoles); quinine salts (bisulfate, sulfate, chloride, oleate, and tannate); derivatives of quinoline (salts of 8-hydroxyquinoline and 2-phenylquinoline); hydroxymethoxy-substituted benzophenones; uric and viloric acids; tannic acid, and derivatives thereof (for example hexaethylether); (butylcarbityl)(6-propylpiperonyl) ether; hydroquinone; benzophenones (oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone, 4-isopropyldibenzoylmethane, butylmethoxydibenzoylmethane; octocrylene; 4-isopropyldibenzoylmethane); derivatives of camphor such as methylbenzylidene or benzylidenecamphor; and analogs thereof, and mixtures thereof.

When they are used in compositions of the present invention, sunscreens represent in the range 0.5% to 50% by weight, total weight of the total weight of the composition, preferably, in the range 0.5% to 30% by weight, and more preferably in the range 0.5% to 20% by weight, relative to the total weight of the composition. The quantity incorporated varies as a function of the sunscreen selected and the desired amount of sun protection factor (SPF) as defined in US application 2003/0147825.

Cleansing Surfactants

Cleansing surfactants that may be incorporated in the composition of the invention include a variety of non-ionic, cationic, anionic and zwitterionic surfactants, such as those described in Mc Cutcheon's Detergents and Emulsifiers, North American Edition (1996), Allured Publishing Corporation, and in U.S. Pat. Nos. 3,755,560; 4,421,769; 4,704, 272; 4,741,855; 4,788,006 and 5,011,681. Examples of suitable surfactants include, but are not limited to, alkyl and alkenyl sulfates, ethoxylated alkyl and alkenyl sulfates (preferably having an average degree of ethoxylation of 1 to 10); succinamate-type surfactants such as alkyl sulfosuccinamates and dialkyl esters of sulfosuccinic acid; neutralized fatty acid esters of isethionic acid; and alkyl and alkenyl sulfonates, such as olefin sulfonates and beta-alkoxy sulfonates; and analogs thereof. Preference is given to alkyl and alkenyl sulfates, ethoxylated alkyl and alkenyl sulfates, for example sodium and ammonium salts of $C_{12}$-$C_{18}$ sulfates and ethoxylated sulfates (preferably having a degree of ethoxylation of 1 to 6, and preferably lying in the range 1 to 4), such as lauryl sulfate and laureth (3.0) sulfate; sodium 3-dodecylaminopro-pionate; N-alkyltaurines such as those prepared by reacting dodecylamine with sodium isethionate according to the teaching of U.S. Pat. No. 2,658,072; (N-higher alkyl) aspartic acids such as those produced according to the teaching of U.S. Pat. No. 2,438,091; and the products sold under the trade name "Miranol" and described in US patent U.S. Pat. No. 2,528,378, and analogs thereof. Other suitable surfactants include $C_6$-$C_{22}$ alkyl amphoglycinates and $C_6$-$C_{22}$ alkyl amphopropionates, and preferably, alkyl amphoglycinates, $C_8$-$C_{12}$ alkyl amphopropionates; zwitteronic cleansing surfactants chosen from aliphatic compounds of quaternary ammonium, of $C_8$-$C_{18}$ phosphonium and sulfonium, that carry a substituent containing a water-soluble anionic group, such as a carboxy, a sulfonate, a sulfate, a phosphate, a phosphonate, and analogs thereof; alkyl aminosulfonates, alkylbetaines and alkylamidobetaines, stearamidopropyldimethylamine, diethylaminoethylstearamide, dimethylstearamine, dimethylsojamine, sojamine, myristylamine, tridecylamine, ethylstearylamine, N-tallowpropanediamine, ethoxylated stearylamine (5 moles of ethylene oxide), dihydroxyethylstearylamine, arachidylbehenylamine, and analogs thereof. When the composition contains one or more cleansing surfactants, they typically represent in the range 0.5% to 20% by weight, and preferably in the range 1% to 12% by weight, relative to the total weight of the composition.

Skin Conditioning Polymers

As examples of skin conditioning polymers that may be incorporated in the composition, mention may be made of quaternized guar gum, quaternized cellulose compounds, polyquaternium-4, polyquaternium-7, polyquaternium-10, polyquaternium-11, polyquaternium-39, polyquaternium-44, and analogs thereof. When the composition contains one or more conditioning polymers, they typically represent in the range 0.01% to 3% by weight, relative to the total weight of the composition, preferably in the range 0.1% to 2% by weight, and more preferably in the range 0.1% to 1% by weight, relative to the total weight of the composition.

Vitamins

As examples of vitamins that may be incorporated in the composition, mention may be made of vitamin A, vitamin B, biotin, pantothenic acid, vitamin C, vitamin D, vitamin E, tocopherol acetate, retinyl palmitate, magnesium ascorbylphosphate, and analogs thereof, and derivatives thereof. When the composition contains one or more vitamins, they typically represent in the range 0.001% to 5% by weight, relative to the total weight of the composition, preferably in the range 0.01% to 2% by weight, and more preferably in the range 0.1% to 1% by weight, relative to the total weight of the composition.

Chelating Agents

As examples of chelating agents that may be incorporated in the composition, mention may be made of EDTA (ethylenediaminetetraacetic acid) and salts thereof such as disodium EDTA; citric acid and salts thereof; cyclodextrines; and analogs thereof. When the composition contains one or more chelating agents, they typically represent in the range 0.001% to 3% by weight, relative to the total weight of the composition, preferably in the range 0.01% to 2% by weight, and more preferably in the range 0.01% to 1% by weight, relative to the total weight of the composition.

Neutralizing Agents and pH Adjusting Agents

Neutralizing agents and pH adjusting agents may be incorporated in the composition in order to bring the pH of the composition to the desired levels. As examples of neutralizing agents and pH adjusting agents mention may be made of triethanolamine, aminomethylpropanol, ammonium hydroxide, sodium hydroxide, other alkali hydroxides, borates, phosphates, pyrophosphates, coco-amine, oleilamine, diisopropanolamine, diisopropylamine, dodecylamine, PEG-15 coco-amine, morphine, tetrakis(hydroxypropyl)ethylenediamine, triamylamine, triethanolamine, triethylamine, tromethamine (2-amino-2-hydroxymethyl-1,3-propanediol), ascorbic acid and salts thereof, sorbic acid and salts thereof, phosphoric acid and salts thereof, citric acid and salts thereof, lactic acid and salts thereof, glycolic acid and salts thereof, boric acid and salts thereof, acetic acid and salts thereof, and analogs thereof. Preferably, neutralizing agents and pH adjusting agents are used in the composition of the invention in an amount that is sufficient for confering a pH lying in the range 4 to 10. Preferably, the pH adjusting agents are used in an amount that is sufficient for confering the composition with a pH lying in the range 4.5 to 8, and preferably in the range 5 to 7.5.

Opacifiers

As examples of opacifiers, mention may be made of glycol fatty acid esters such as glycol dibehenate, glycol dioleate, glycol distearate, glycol dilallowate, glycol hydroxystearate, glycol montanate, glycol palmitate and glycol stearate; fatty acids and hydrogenated fatty acid mixtures such as behenic acid, arachidic acid, palmitic acid, myristic acid, corn (maize) acid, palm acid, palm bark acid, hydrogenated coprah acid, hydrogenated menhaden acid, hydrogenated palm acid, hydrogenated tallow acid, alkoxylated fatty acid esters; silica; alkanolamides such as behenamide, linoleamide and stearamide; talc; Nylon; fatty acid alcohols such as arachidyl alcohol, behenic alcohol, stearyl alcohol, cetyl alcohol, and myristyl alcohol; waxes and oils; kaolin; magnesium silicate; and analogs thereof. When they are present in the compositions, opacifier(s) typically represent(s) lying in the range 0.1% to 8% by weight, relative to the total weight of the composition, preferably, lying in the range 0.5% to 6% by weight, and more preferably lying in the range 1% to 5% by weight, relative to the total weight of the composition of the present invention.

Preservatives

As examples of preservatives, mention may be made of polymethoxy bicyclic oxazolidine, methylparaben, propylparaben, ethylparaben, butylparaben, benzoic acid and salts of benzoic acid, benzyltriazole, DMDM-hydantoin (also known by the name 1,3-dimethyl-5,5-dimethyl-hydantoin), imidaolidinyl urea, phenoxyethanol, phenoxyethylparaben, methylisothiazolinone, methylchloroisothiazolinone, benzoisothiazolinone, triclosan, sorbic acid, salts of salicylic acid, and analogs thereof. When they are present in the composition, (a) preservative(s) typically represent(s) lying in the range 0.01% to 1.5% by weight, relative to the total weight of the composition, preferably lying in the range 0.1% to 1% by weight, and more preferably lying in the range 0.3% to 1% by weight, relative to the total weight of the composition.

Leveling Agents

As examples of leveling agents, mention may be made of hydroxypropylmethylcellulose, cellulose compounds modified to be hydrophobic, xanthan gum, acacia gum, guar gum, locust bean gum, dimethiconecopolyols having various degrees of alkoxylation, aluminum-magnesium silicate, boron nitride, talc, and analogs thereof. When they are present in the composition, the leveling agent(s) typically represent(s) lying in the range 0.01% to 1.5% by weight, relative to the total weight of the composition, preferably lying in the range 0.1% to 3% by weight, and more preferably lying in the range 0.1% to 2% by weight, relative to the total weight of the composition.

Furthermore, the invention is particularly adapted to compositions comprising an electrolyte, which may be defined as a positively or negatively-charged chemical substance that is capable of transporting or conducting an electric charge, generally in a solution. They are also referred to as ionic compounds and, in the field of cosmetic and dermatological composition formulation, as ionic ingredients. They may be monovalent or multivalent. Electrolytes are principally acids, bases, or salts. More precisely, among the electrolytes often found in cosmetic and dermatological compositions mention can be made of admixtures/adjuvants such as vegetable extracts containing monovalent or divalent ions such as fruit acids, active principles such as hydroxy acids for their anti-ageing effect, moisturizing agents such as pyrrolidone carboxylic acid (PCA), chelating agents such as for example ethylenediaminetetraacetic acid (EDTA), UV filters such as phenylbenzimidazole sulfonic acid, certain preservatives, or also salts such as alum salt.

A topical composition of the invention may be for cosmetic use, excluding any therapeutic treatment, or it may be used as a medication for treating diseases of the skin and the mucous membranes. In the latter example, the topical composition thus includes at least one active pharmaceutical principle, by way of example chosen from anti-fungal agents, anti-bacterial agents, anti-inflammatory agents, myorelaxants, antibiotics, antiviral agents, analgesics (for example ibuprofen, acetylsalicylic acid, naproxen, and analogs thereof), anti-histamines, antipruritic agents, antipyretic agents, anesthetic agents, diagnostic agents, hormones, skin growth enhancers, pigment modulators, antiproliferative agents, antipsoriatic agents, retinoids, anti-acne drugs (for example benzoyl peroxide, sulfur, and analogs thereof), antineoplastic agents, phototherapeutic agents, keratolytic agents (for example resorcinol, salicylic acid, and analogs thereof), and analogs thereof. Naturally, the person skilled in art will adapt the amount of said optional additional compound(s) in order to obtain the desired effect.

The thickening acrylic polymers used in the context of the invention may be used in the applications described in patent application EP 1 710 259 in the name of SEPPIC. Also, they may be associated with fatty acid esters and sugar esters in order to form compositions for treating the hair or the skin such as those described in EP 0 603 019, or also in shampoos or conditioners as described and claimed in WO 92/21316, or, finally, in association with an anionic homopolymer such as a CARBOPOL in order to form products for treating hair such as those described in DE 195 23 596.

The thickening acrylic polymers used in the context of the invention also are compatible with the active principles such as for example, the self-tanning agents such as dihydroxyacetone (DHA) or anti-acne agents; it can therefore be introduced into self-tanning compositions such as those claimed in EP 0 715 845, EP 0 604 249, EP 0 576 188, or in WO 93/07902.

The thickening acrylic polymers used in the context of the invention are also compatible with the N-acyl derivatives of amino acids, and may therefore be used in soothing compositions in particular for sensitive skin, such as those described or claimed in WO 92/21318, WO 94/27561, or WO 98/09611.

The cosmetic compositions of the invention may be in the form of a care product and/or of makeup for the skin of the body or face, lips, and hair; of a sunscreen or self-tanning product; of a hair product such as shampoos, gels, setting lotions, blow-dry lotions.

In a preferred embodiment, the compositions of the invention may be used for washing or treatment, in particular cosmetic washing or treatment, of keratinous material such as hair, skin, eyelashes, eyebrows, nails, lips, scalp, and more particularly hair.

The compositions of the invention may be detergent compositions such as shampoos, shower gels, and bubble baths. In this embodiment of the invention, the compositions comprise at least one washing base that is generally aqueous.

The invention therefore provides a process for treating keratinous material such as the skin or the hair, the process being characterized in that it consists in applying a cosmetic composition as defined above to keratinous material, and then possibly rinsing with water.

The examples given below make it possible to illustrate the invention, but are not limited thereto.

I. EXAMPLES OF PREPARATION OF ACRYLIC ACID/SODIUM ACRYLATE-BASED HOMOPOLYMER

Example 1

The ingredients of the aqueous phase were loaded in a 1 L beaker with magnetic stirring:
  150 g of glacial acrylic acid
  605 g of deionized water
  0.023 g of sodium hypophosphite (150 ppm/total weight of monomers)
  0.10 g of sodium diethylenetriaminepentaacetate
  0.075 g of methylenebisacrylamide (500 ppm/total weight of monomers)
  0.15 g of sodium bromate.

Next, in a 1 L glass reactor, with magnetic stirring, the organic phase was prepared with:
  102 g of aliphatic hydrocarbon (Isopar L)
  98 g of white mineral oil (Marcol 152)
  20 g of sorbitol monooleate
  25 g of polymeric stabilizer (Hypermer 1083).

The aqueous phase was gradually transferred into the organic phase. The pre-emulsion thus formed was then subjected to strong shearing for 1 minute (Ultra Turrax, IKA).

The inverse emulsion was then degassed for 30 minutes by means of simple nitrogen sparging.

An aqueous solution containing 1.0% by weight of sodium metabisulfite was then added at a flow rate of 2.5 mL/h for a period of 1 h 30. Once the maximum temperature has been reached, the temperature of the reaction mixture was maintained for 60 minutes before cooling.

Finally, 40 g of ethoxylated (6 mol) tridecyl alcohol were added at around 30° C.

Example 2

The ingredients of the aqueous phase were loaded in a 1 L beaker with magnetic stirring:
  175 g of glacial acrylic acid
  580 g of deionized water 0.026 g of sodium hypophosphite (150 ppm/total weight of monomers)
0.10 g of sodium diethylenetriaminepentaacetate
0.087 g of methylenebisacrylamide (500 ppm/total weight of monomers)
0.15 g of sodium bromate.

Next, the preparation of the organic phase and the rest of the preparation process were carried out in accordance with Example 1.

Example 3

The ingredients of the aqueous phase were loaded in a 1 L beaker with magnetic stirring:
100 g of glacial acrylic acid
655 g of deionized water
0.015 g of sodium hypophosphite (150 ppm/total weight of monomers)
0.10 g of sodium diethylenetriaminepentaacetate
0.05 g of methylenebisacrylamide (500 ppm/total weight of monomers)
0.15 g of sodium bromate.

Next, the preparation of the organic phase and the rest of the preparation process were carried out in accordance with Example 1.

Example 4

Neutralization 3.5%/Concentration 2.76

The same process as in Example 1 was carried out, with 5.83 g of 50% sodium hydroxide solution being added to the aqueous phase, while at the same time maintaining the same weight of aqueous phase by adjusting the amount of deionized water.

Example 5

Neutralization 19%/Concentration 3.5

The ingredients of the aqueous phase were loaded in a 1 L beaker with magnetic stirring:
190 g of glacial acrylic acid
40 g of 50% sodium hydroxide solution
525 g of deionized water
0.028 g of sodium hypophosphite (150 ppm/total weight of monomers)
0.10 g of sodium diethylenetriaminepentaacetate
0.095 g of methylenebisacrylamide (500 ppm/total weight of monomers)
0.15 g of sodium bromate.

Next, the preparation of the organic phase and the rest of the preparation process were carried out in accordance with Example 1.

Example 6

The ingredients of the aqueous phase were loaded in a 1 L beaker with magnetic stirring:
150 g of glacial acrylic acid
605 g of deionized water
0.10 g of sodium diethylenetriaminepentaacetate
0.225 g of methylenebisacrylamide (1500 ppm/total weight of monomers)
0.15 g of sodium bromate.

Next, in a 1 L glass reactor, with magnetic stirring, the organic phase was prepared with:

102 g of aliphatic hydrocarbon (Isopar L)
98 g of white mineral oil (Marcol 152)
20 g of sorbitol monooleate
25 g of polymeric stabilizer (Hypermer 1083).

The aqueous phase was gradually transferred into the organic phase. The pre-emulsion thus formed was then subjected to strong shearing for 1 minute (Ultra Turrax, IKA).

The inverse emulsion was then degassed for 30 minutes by means of simple nitrogen sparging.

An aqueous solution containing 1.0% by weight of sodium metabisulfite was then added at a flow rate of 2.5 mL/h for a period of 1 h 30. Once the maximum temperature has been reached, the temperature of the reaction mixture was maintained for 60 minutes before cooling.

Finally, 40 g of ethoxylated (6 mol) tridecyl alcohol were added at around 30° C.

Comparative Example 1

The ingredients of the aqueous phase were loaded in a 1 L beaker with magnetic stirring:
50 g of glacial acrylic acid
705 g of deionized water
0.075 g of sodium hypophosphite (150 ppm/total weight of monomers)
0.10 g of sodium diethylenetriaminepentaacetate
0.043 g of methylenebisacrylamide (860 ppm/total weight of monomers)
0.15 g of sodium bromate.

Next, the preparation of the organic phase and the rest of the preparation process were carried out in accordance with Example 1.

Comparative Example 2

The ingredients of the aqueous phase were loaded in a 1 L beaker with magnetic stirring:
199 g of glacial acrylic acid
115 g of 50% sodium hydroxide solution
441 g of deionized water
0.03 g of sodium hypophosphite (150 ppm/total weight of monomers)
0.10 g of sodium diethylenetriaminepentaacetate
0.15 g of methylenebisacrylamide (750 ppm/total weight of monomers)
0.15 g of sodium bromate.

Next, the preparation of the organic phase and the rest of the preparation process were carried out in accordance with Example 1.

Comparative Example 3

The ingredients of the aqueous phase were loaded in a 1 L beaker with magnetic stirring:
199 g of glacial acrylic acid
556 g of deionized water
0.03 g of sodium hypophosphite (150 ppm/total weight of monomers)
0.10 g of sodium diethylenetriaminepentaacetate
0.1 g of methylenebisacrylamide (500 ppm/total weight of monomers)
0.15 g of sodium bromate.

Next, the preparation of the organic phase was carried out in accordance with Example 1.

The aqueous phase was gradually transferred into the organic phase. The pre-emulsion thus formed was then subjected to strong shearing for 1 minute (Ultra Turrax, IKA).

The inverse emulsion was then degassed for 30 minutes by means of simple nitrogen sparging.

An aqueous solution containing 1.0% by weight of sodium metabisulfite was then added at a flow rate of 2.5 mL/h. Immediately after the beginning of the addition of this reducing solution, the emulsion was destabilized and then coagulated. Polymerization was impossible, the system was not stable.

Comparative Example 4

The ingredients of the aqueous phase were loaded in a 1 L beaker with magnetic stirring:
150 g of glacial acrylic acid
83 g of 50% sodium hydroxide solution
522 g of deionized water
0.023 g of sodium hypophosphite (150 ppm/total weight of monomers)
0.10 g of sodium diethylenetriaminepentaacetate
0.75 g of methylenebisacrylamide (500 ppm/total weight of monomers)
0.15 g of sodium bromate.

Next, the preparation of the organic phase and the rest of the preparation process were carried out in accordance with Example 1.

Polymer Characterization

Process: Measurement of the viscosity of the aqueous solution of polymer at isoconcentration [0.16% by weight]

250 g of deionized water were placed in a 400 mL beaker and then, with mechanical stirring (three-blades—500 rpm), the desired amount of inverse emulsion was gradually added so as to obtain a solution containing 0.16% by weight of active polymer. The pH was then adjusted to 7±0.1 with sodium hydroxide. At this pH, 100% of the acid functions present on the polymer were neutralized. The solution was stirred for 15 minutes and then left to stand for 5 minutes. The viscosity was then measured using a Brookfield RVT viscometer with module 4 and a rotational speed of 20 rpm.

The results are recorded in Table 1.

TABLE 1

| Example | AFN | MC | Viscosity 0.16% in water (centipoise (cps)) |
|---|---|---|---|
| 1 | 0% | 2.8 | 6500 |
| 2 | 0% | 3.2 | 4000 |
| 3 | 0% | 1.8 | 6200 |
| 4 | 3.5% | 2.8 | 6500 |
| 5 | 19% | 3.5 | 2500 |
| 6 | 0% | 2.8 | 15000 |
| Comparative 1 | 0% | 0.9 | 1700 |
| Comparative 2 | 52% | 3.7 | 500 |
| Comparative 3 | 0% | 3.7 | Emulsion not stable |
| Comparative 4 | 50% | 2.8 | 1500 |
| ET75 | 50% | 3.8 | 50 |

AFN: Acid function neutralization (%) at the end of polymerization
MC: Monomer concentration in mmol/g of aqueous phase ET75 is a commercial inverse emulsion of acrylic acid homopolymer, of which 50% of the acid functions were neutralized before polymerization.

The polymers used in the context of the invention obtained by means of the inverse emulsion polymerization process have a much better thickening effect than the polymers obtained by means of inverse emulsion processes which do not comply with the conditions for percentage neutralization before polymerization and monomer concentration.

The polymers obtained in the invention are very effective at very low concentration.

The resistance to electrolytes was evaluated by using said same polymers in deionized water and in the presence of an electrolyte, the ethylenediaminetetraacetic acid (EDTA).

The polymers were compared to one another and to other commercially-available thickening polymers. Those polymers were Sepigel® 305 (SEPPIC) and Novemer® EC2 (Noveon), which are inverse emulsions, and Carbopol® 980 (Lubrizol), which is a crosslinked acrylic acid polymer obtained by precipitation polymerization. Said commercial products are typically used in cosmetic or dermatological compositions as a thickener.

The variation in the viscosity of a solution including 0.5% by weight thickening polymer was studied as a function of the concentration in EDTA.

More precisely, 250 g of deionized water were placed in a 400 mL beaker and then, with mechanical stirring (three-blades—500 rpm), the desired amount of inverse emulsion was gradually added so as to obtain a solution containing 0.5% by weight of active polymer. The pH was then adjusted to 7±0.1 with sodium hydroxide. At this pH, 100% of the acid functions present on the polymer were neutralized. An aqueous solution of EDTA (5% by weight) was added at the desired concentration. The solution was stirred for 15 minutes and then left to stand for 5 minutes. The viscosity was then measured using a Brookfield RVT viscometer with module 4 and a rotational speed of 20 rpm.

The results are recorded in Table 2.

TABLE 2

Viscosity measurements of a solution containing 0.5% by weight of polymer with added EDTA

| Ex | AFN (%) | MC (mmol/g) | Viscosity (cps) | | | | |
|---|---|---|---|---|---|---|---|
| | | | 0% EDTA | 0.025% EDTA | 0.05% EDTA | 0.1% EDTA | 0.2% EDTA |
| 1 | 0% | 2.8 | 13500 | 13000 | 12000 | 11000 | 9200 |
| 2 | 0% | 3.2 | 16000 | 14000 | 12000 | 10250 | 7500 |
| 3 | 0% | 1.8 | 11500 | 11000 | 10250 | 9750 | 9000 |
| 4 | 3.5% | 2.8 | 14000 | 13000 | 12000 | 11250 | 9500 |

TABLE 2-continued

Viscosity measurements of a solution
containing 0.5% by weight of polymer with added EDTA

| | | | Viscosity (cps) | | | | |
|---|---|---|---|---|---|---|---|
| Ex | AFN (%) | MC (mmol/g) | 0% EDTA | 0.025% EDTA | 0.05% EDTA | 0.1% EDTA | 0.2% EDTA |
| 5 | 19% | 3.5 | 18000 | 12000 | 7500 | 5000 | 3500 |
| 6 | 0% | 2.8 | 35000 | 32000 | 29500 | 23500 | 14000 |
| Comp. 1 | 0% | 0.9 | 5500 | 2500 | 1500 | 950 | 450 |
| Comp. 2 | 52% | 3.7 | 20000 | 14000 | 5000 | 800 | <50 |
| Comp. 3 | 0% | 3.7 | NA | NA | NA | NA | NA |
| Comp. 4 | 50% | 2.8 | 16000 | 12000 | 6000 | 750 | 300 |
| Sepigel® 305 | | | 10000 | 5000 | <50 | <50 | <50 |
| Novemer® EC2 | | | 20800 | 19000 | 16400 | 12700 | 7300 |
| Carbopol® 980 | Not applicable because of different polymerization methods | | 39000 | 32000 | 26000 | 17000 | 8000 |

AFN: Acid function neutralization (%) at the end of polymerization
MC: Monomer concentration in mmol/g of aqueous phase

TABLE 3

Percentage of viscosity maintained with addition of EDTA
The percentage of viscosity maintained corresponds
to the ratio between the final viscosity in the presence
of EDTA and the initial viscosity without EDTA multiplied by 100.

| Ex | 0.025% EDTA | 0.05% EDTA | 0.1% EDTA | 0.2% EDTA |
|---|---|---|---|---|
| 1 | 96% | 89% | 82% | 68% |
| 2 | 88% | 75% | 64% | 47% |
| 3 | 96% | 89% | 85% | 78% |
| 4 | 93% | 86% | 80% | 68% |
| 5 | 67% | 42% | 28% | 19% |
| 6 | 91.4% | 84.3% | 67.1% | 40% |
| Comp. 1 | 45% | 27% | 17% | 8% |
| Comp. 2 | 70% | 25% | 4% | <0.25% |
| Comp. 3 | NA | NA | NA | NA |
| Comp. 4 | 75% | 38% | 5% | 2% |
| Sepigel® 305 | 50% | <0.5% | <0.5% | <0.5% |
| Novemer® EC2 | 91% | 79% | 61% | 35% |
| Carbopol® 980 | 82% | 66.7% | 43.6% | 20.5% |

The polymers of examples 1 to 6 serve to obtain a very good, or even excellent resistance to electrolytes compared with the polymers of the comparative examples 1 to 4.

When examples 1 to 6 are compared, it is observed that the polymer providing the better thickening effectiveness without electrolytes (polymer 6) is a little less resistant to electrolytes than polymer 1. The expertise of the person skilled in the art makes it easy to find the best compromise between thickening effectiveness and resistance to electrolytes by varying polymerization parameters.

Sepigel® 305 procures an advantageous thickening effect, but has a very low resistance to electrolytes.

Novemer® EC2 serves to obtain both good thickening and a satisfactory resistance to electrolytes, but it leads to a texture that is somewhat structured, or even gelled, that does not correspond to consumer expectations, as explained in the portion relating to examples of cosmetic and dermatological compositions.

Carbopol® 980 has very good thickening effectiveness that is comparable to that of the polymer of example 6. Nevertheless, its resistance to electrolytes is lower than that of the polymer of example 6.

II. Comparative Study Relative to the Inverse Emulsion Processes and Polymers Proposed in the Prior Art The thickening effect of polymers obtained by inverse emulsion polymerization, as described in the prior art, and of polymers obtained according to the invention, all other conditions being otherwise equal, was compared.

The examples of various prior art documents were reproduced and then only the concentration and/or the percentage neutralization was(were) modified in order to correspond to the invention. Next, the inverse emulsions were used and the viscosities were measured according to the same protocol as that described previously.

In what follows, AA denotes acrylic acid, AM denotes acrylamide and ATBS denotes 2-acrylamido-2-methylpropanesulfonic acid.

a. EP 0 503 853

Examples 2 and 7 described on pages 5-6 of patent EP 0 503 853 were reproduced. These Examples 1, 2 and 7 were then modified in order to correspond to the invention. Only the concentration and/or the percentage neutralization was (were) modified in order to correspond to the invention. Next, the inverse emulsions were used and the viscosities were measured according to the same protocol as that described previously.

In what follows, AA denotes acrylic acid, AM denotes acrylamide.

Example 7

Example 7 corresponds to Example 2 in which the amounts of acrylic acid monomer, of NaOH and of MBA were reduced and replaced with deionized water so as to obtain the same amount of aqueous phase, a total concentration of monomers of 3.4 mmol/g of aqueous phase, instead of 4.3, and an acid function neutralization of 15% instead of 100%.

Example 8

Example 8 corresponds to Example 7 in which the amounts of acrylamide and acrylic acid monomers and of MBA and also of NaOH were reduced and replaced with deionized water so as to obtain a total concentration of monomers of 3.4 mmol/g of aqueous phase, instead of 4.3, and an acid function neutralization of 15% instead of 100%.

The results are recorded in Table 4.

TABLE 4

| Example | Acid function neutralization (%) | Monomer(s) ratio (mol %) | [monomer(s)] mmol/g aqueous phase | Viscosity 0.16% in water (cps) |
|---|---|---|---|---|
| Ex 2 from EP 0 503 853 | 100% | AA: 100% with branching agent | 4.3 | 20 |
| 7 | 15% | AA: 100% with branching agent | 3.4 | 6500 |
| Ex 7 from EP 0 503 853 | 100% | AM: 50% AA: 50% with branching agent | 4.3 | 50 |
| 8 | 15% | AM: 50% AA: 50% with branching agent | 3.4 | 4500 |

The combination of the two essential characteristics of the invention, for preparing the polymers used in the context of the invention, namely a low-concentration of monomers in the aqueous phase combined with a low degree of neutralization of the monomers comprising acid functions makes it possible to obtain polymers which provide a greatly improved thickening effect.

The resistance to electrolytes of prior art polymers that are not very viscosifying (only 20 cps to 50 cps at 0.16%) has not been tested since said polymers present little advantage relative to their equivalents prepared in the conditions used in the context of the invention. Furthermore, Sepigel® 305 from the supplier SEPPIC corresponds to the invention defined in patent EP 0 503 853 and the above shows that said polymer has low resistance to electrolytes.

b. WO 2005/097834

Example 2 described on page 14 of patent WO 2005/097834 was reproduced. The percentage neutralization and the monomer concentration were then lowered in order to correspond to the invention (Example 9).

The results are recorded in Table 5.

TABLE 5

| Example | Neutralization | Monomer ratio (mol %) | [monomer] mmol/g aqueous phase | Viscosity 0.16% in water (cps) |
|---|---|---|---|---|
| Ex 2 from WO 2005/097834 | 37.5% | AA: 100% | 4.7 | 20 |
| Example 9 | 18% | AA: 100% | 3.4 | 2500 |

Once again, these tests show the advantage of using polymers prepared in accordance with the invention compared with the prior art processes, since it makes it possible to considerably improve the thickening capacity of the polymers obtained.

III—Effectiveness and Appearance in Cosmetic and Dermatological Compositions The following tests show the advantage of using the polymers obtained in the conditions of concentration and percentage neutralization, defined in the context of the invention in cosmetic or dermatological compositions. Such polymers provide not only good thickening of compositions, including in the presence of electrolytes, but they also procure an appearance that is attractive both to the touch and on application.

Creams, lotions, and cosmetic or dermatological gels containing electrolytes were formulated with inverse emulsions of examples 1 to 6 and Novemer® EC2.

For each of the compositions numbered 1 to 3 below, the preparation protocol applied was as follows:

Preparation of Part A:

Deionized water was added to a 400 mL beaker

While stirring with a deflocculation blade at 500 rpm, the inverse emulsion was added The pH was adjusted to within the desired range by means of sodium hydroxide or citric acid, put into an aqueous solution at 10% and 50% respectively.

The other ingredients were added 15 minutes of stirring was sufficient to obtain a homogenous viscous paste Preparation of Part B:

The ingredients were mixed in a 400 mL beaker

Stirring using three blades for 5 minutes at 250 rpm was sufficient to ensure that the mixture was homogeneous.

At ambient temperature, part B was transferred progressively into part A. Stirring was then increased to 2000 rpm for 10 minutes.

The formulation was then left to rest for 60 minutes before checking the viscosity by means of an RTV viscosimeter, 20 rpm, module 6.

Composition No 1: Gel-cream Base

| Ingredients (100 parts) | Example 1 | Novemer ® EC 2 | Example 6 |
|---|---|---|---|
| Part A: | | | |
| Deionized water | 75.0 | 75.0 | 75.0 |
| EDTA (aqueous solution at 5% by weight) | 2.0 | 2.0 | 2.0 |
| Polymer* | 2.1 (1) | 7.5 (1.5) | 0.9 (0.42) |
| Sodium hydroxide | 1.3 | — | 0.65 |
| Citric acid | — | 1.4 | — |
| Part B: | | | |
| Deionized water | 17.25 | 11.75 | 19.1 |
| Glycerine @ 85% | 2.35 | 2.35 | 2.35 |

-continued

| Ingredients (100 parts) | Example 1 | Novemer ® EC 2 | Example 6 |
|---|---|---|---|
| Results: | | | |
| pH | 5.4 | 5.4 | 5.5 |
| Final viscosity in cps | 21500 | 22500 | 20200 |

*Polymer in the form of inverse emulsion or commercial polymer for Novemer ® EC2. The percentage polymer in the inverse emulsion of example 1 was 47.6%, in the inverse emulsion of example 6 it was 46.4%, and for Novemer ® EC2 it was 20%. The percentage of polymer by weight in the composition is written in brackets.

Polymers used in the context of the invention make it possible to effectively viscosify the gel cream base even if it contains 0.1% of EDTA. They make it possible to use less polymer for thickening the gel cream base to a standard viscosity of about 20000 cps: 1% of the polymer of example 1 or 0.42% of the polymer of example 6 instead of 1.5% of Novemer® EC2, i.e. respective reductions in quantity of 33% and of 72%, which is very significant.

In addition, the gel cream base obtained with the polymers of examples 1 to 6 has a very attractive appearance. On application to the skin it feels soft and pleasant, unlike the base obtained with Novemer® EC2 which, being more structured, provides a somewhat unpleasant sensation.

An additional test was carried out using polymers 1 and 6 in powder form, instead of the inverse emulsion version. More precisely, polymers 1 to 6 in powder form, obtained from the inverse emulsions, were put into solution in water, said solution being added to the composition gel cream base to be thickened. The viscosity and texture results were substantially the same as those obtained with inverse emulsions.

Composition No 2: Silicone-based Lotion

| Ingredients (100 parts) | Example 1 | Novemer ® EC 2 | Example 6 |
|---|---|---|---|
| Part A: | | | |
| Deionized water | 76.6 | 70.2 | 77.2 |
| EDTA (aqueous solution at 5% by weight) | 2 | 2 | 2 |
| Polymer* | 3.3 (1.57) | 12.5 (2.5) | 3.4 (1.58) |
| Sodium hydroxide | 3.1 | — | 2.35 |
| Citric acid | — | 0.3 | — |
| Part B: | | | |
| Dimethicone | 10 | 10 | 10 |
| Octyl palmitate | 5 | 5 | 5 |
| Results: | | | |
| pH | 5.9 | 6.0 | 5.9 |
| Final viscosity in cps | 11600 | 9000 | 11200 |

Polymers used in the context of the invention make it possible to effectively viscosify the silicone-based lotion even if it contains 0.10 of EDTA. They make it possible to use less polymer for thickening the lotion to a standard viscosity of about 10 000 cps: 1.570 of the polymer of example 1 or 1.580 of the polymer of example 6 instead of 2.5% of Novemer® EC2, i.e. a reduction in quantity of 37%, which is very significant.

In addition, the lotion obtained with the polymers of examples 1 and 6 is very attractive in appearance. On application to the skin it feels soft and pleasant, unlike the base obtained with Novemer® EC2 which, more structured, provides a somewhat unpleasant sensation.

Composition No 3: Base for Hair Cream

| Ingredients (100 parts) | Example 1 | Novemer ® EC 2 | Example 6 |
|---|---|---|---|
| Part A: | | | |
| Deionized water | 92.4 | 90.2 | 92.75 |
| EDTA (aqueous solution at 5% by weight) | 2 | 2 | 2 |
| Polymer* | 1.0 (0.48) | 3.5 (0.7) | 0.75 (0.35) |
| Sodium hydroxide | 0.6 | — | 0.5 |
| Citric acid | — | 0.3 | — |
| Part B: | | | |
| Olive oil | 4 | 4 | 4 |
| Results: | | | |
| pH | 5.5 | 5.6 | 5.5 |
| Final viscosity in cps | 12000 | 13300 | 11500 |

The polymers used in the context of the invention make it possible to effectively viscosify the cream even if it contains 0.1% of EDTA. They make it possible to use less polymer for thickening the cream to a standard viscosity of about 12 000 cps: 0.48% of the polymer of example 1 or 0.35% of the polymer of example 6 instead of 0.7% of Novemer® EC2, i.e. respective reductions in quantity of 31% and of 50%, which is very significant.

In addition, the cream obtained with the polymers of examples 1 and 6 has a very attractive appearance. On application to the skin it feels soft and pleasant, unlike the base obtained with Novemer® EC2 which, more structured, provides a somewhat unpleasant sensation.

Composition No 4: Shampoo

The procedure consisted firstly in dispersing the polymer in the deionized water stirred by three blades at 300 rpm. Propylene glycol, and the surfactant were then added. After adjusting the pH, betaine was added slowly while stirring. The final formulation was then stirred for 30 minutes.

| Ingredients (100 parts) | Example 1 | Carbopol ® 980 |
|---|---|---|
| Deionized water | 57.9 | 58.9 |
| Polymer | 2.0 | 1.0 |
| Propylene glycol | 6.0 | 6.0 |
| Sodium Laureth Sulfate 3EO (28%) | 30.0 | 30.0 |
| Disodium EDTA | 0.1 | 0.1 |
| NaOH | QSP pH = 6.7 ± 0.2 | |
| Cocamidopropyl betaine | 4.0 | 4.0 |
| Results: | | |
| pH | 6.7 | 6.8 |
| LVT Viscosity, 30 rpm | 6500 cps | 2500 cps |

The polymer used in the context of the invention makes it possible to effectively viscosify a formulation containing detergent surfactants. The formulation is stable and presents excellent flow characteristics.

Composition No 5: Base for Shower Gel

The procedure was the same as for example 4 with the following composition:

| Ingredients (100 parts) | Example 1 | Carbopol ® 980 |
|---|---|---|
| Deionized water | | |
| Polymer | 2.0 | 1.0 |
| Sodium Laureth Sulfate 2EO (28%) | 32.0 | 32.0 |
| NaOH | QSP pH = 5.5 ± 0.2 | |
| Cocamidopropyl betaine | 7.0 | 4.0 |
| Glycerine | 1.5 | 1.5 |
| Polyquaternium-7 | 1.0 | 1.0 |
| Results: | | |
| pH | 5.4 | 5.5 |
| LVT Viscosity, 30 rpm | 3500 cps | 1500 cps |

The polymer used in the context of the invention makes it possible to obtain a formulation that is compatible with all of the other ingredients (in particular with the betaines and the conditioners) in a viscosity range that facilitates application.

The invention claimed is:

1. A method for producing a cosmetic or dermatological composition comprising at least one aqueous phase and a branched or crosslinked polymer composed of the repetition of one or more monomeric units, with at least one of the monomeric units corresponding to a monomer comprising an acrylic group, and at least 30 mol % of the monomeric units bearing at least one weak acid function, at least partially in neutralized form, the percentage of neutralized acid functions relative to all the acid functions present on the polymer being lying in the range 30% to 100%, said method comprising:
  polymerizing an aqueous solution of one or more monomers in water-in-oil inverse emulsion, at least one of the monomers used being an acrylic monomer and one or more of the monomers used being a monomer bearing at least one weak acid function, the molar percentage of monomers bearing at least one weak acid function relative to all of the monomers used being at least 30%, the aqueous phase containing at least one monomer acting as branching agent, in such a manner that polymerization leads to a branched or crosslinked polymer, wherein:
  i) the polymerization is carried out with a concentration of all the monomers in aqueous solution lying in the range 1.3 mmol to 3.6 mmol per gram of aqueous solution; and
  ii) during the polymerization, at most 20% of the acid functions present on the monomers having at least one acid function are in neutralized form;
  the polymerization being followed by a step of at least partial neutralization of the acid functions present, carried out before or after incorporation of the polymer in the composition.

2. The method according to claim 1, wherein, during polymerization, at most 10% of the acid functions present on the monomers having at least one acid function are in neutralized form.

3. The method according to claim 1, wherein all of the acid functions present on the monomers are in free acid form during the polymerization.

4. The method according to claim 1, wherein the polymerization is carried out with a concentration of all the monomers in aqueous solution lying in the range 1.7 to 3.3 mmol per gram of aqueous solution.

5. The method according to claim 1, wherein the polymer includes a molar percentage of monomeric units bearing one or more weak acid function(s), relative to all of the monomeric units bearing an acid function, of at least 50%.

6. The method according to claim 1, wherein all the monomers used for polymer preparation are monomers which have at least one ethylenically unsaturated bond.

7. The method according to claim 1, wherein the monomeric unit(s) bearing at least one weak acid function, in free form, is/are chosen from acrylic acid, methacrylic acid, itaconic acid, crotonic acid, maleic acid, and fumaric acid.

8. The method according to claim 1, wherein the polymer is a copolymer including at least one neutral monomeric unit chosen from acrylamide, methacrylamide, N,N-dimethylacrylamide, N-vinylmethylacetamide, N-vinylformamide, vinyl acetate, diacetone acrylamide, N-isopropylacrylamide, N-[2-hydroxy-1,1-bis(hydroxymethyl)ethyl]propenamide, (2-hydroxyethyl) acrylate, (2,3-dihydroxypropyl) acrylate, methyl methacrylate, (2-hydroxyethyl) methacrylate, (2,3-dihydroxypropyl) methacrylate, and vinylpyrrolidone.

9. The method according to claim 1, wherein all of the monomeric units bearing at least one acid function are monomeric units bearing one or more weak acid function(s).

10. The method according to claim 1, wherein the acrylic monomer is acrylamide and the monomer bearing at least one weak acid function is acrylic acid.

11. The method according to claim 1, further comprising polymerizing at least one monomeric unit bearing one or more strong acid function(s) with the acrylic monomer and the monomer bearing at least one weak acid function.

12. The method according to claim 11, wherein the molar percentage in monomeric units bearing one or more strong acid function(s) relative to all of the monomeric units is less than 50%.

13. The method according to claim 11, wherein the monomeric unit(s) bearing one or more strong acid function(s), in free form, is/are chosen from acrylamidoalkylsulfonic acids.

14. The method according to claim 11, wherein the polymer present in the composition is a copolymer of 2-acrylamido-2-methylpropane sulfonic acid and acrylic acid or of 2-acrylamido-2-methylpropane sulfonic acid and acrylic acid and acrylamide.

15. The method according to claim 1, wherein the branching agent is chosen from methylenebisacrylamide (MBA), ethylene glycol diacrylate, polyethylene glycol dimethacrylate, diacrylamide, cyanomethyl acrylate, vinyloxyethyl acrylate, vinyloxy methacrylate, triallylamine, formaldehyde, glyoxal, glycidyl ethers, and epoxies, and mixtures thereof.

16. The method according to claim 1, wherein the amount of branching agent is between 5 ppm and 10000 ppm by weight, relative to the total weight of monomer.

17. The method according to claim 1, wherein the polymerization reaction is carried out in the presence of a water-in-oil emulsifier.

18. The method according to claim 1, wherein the polymerization is carried out with a transfer agent chosen from methanol, isopropyl alcohol, sodium hypophosphite, 2-mercaptoethanol, and sodium methallyl sulfonate, and mixtures thereof.

19. The method according to claim 18, wherein the amount of transfer agent is between 10 ppm and 5000 ppm by weight, relative to the total weight of monomer.

20. The method according to claim 1, wherein the polymerization is followed by one or more of the following steps:
 diluting or concentrating the resulting emulsion; and
 isolating to obtain the polymer in the form of a powder.

21. The method according to claim 1, wherein, when the branched or crosslinked polymer introduced into the composition is at 0.16% by weight in demineralized water at pH that was adjusted to 7±0.1 with sodium hydroxide, it presents viscosity as measured at 25° C. with a Brookfield viscometer of the RVT type (rotation speed 20 t/min), lying in the range 2000 mPa·s to 100 000 mPa·s.

22. The method according to claim 1, wherein the composition is in the form of a milk, a lotion, a gel, a cream, a gel cream, a soap, a bubble bath, a balm, a shampoo, or a conditioner.

23. The method according to claim 1, wherein the composition comprises an electrolyte, active ingredients for their anti-ageing effect, moisturizing agents, chelating agents, UV filters, preservatives, or salts.

24. The method according to claim 8, wherein the composition comprises in the range 0.01% to 10% by weight of branched or crosslinked polymer, relative to the total weight of the composition.

25. The method according to claim 1, wherein the composition comprises at least one active agent chosen from moisturizing agents, tanning agents, sunscreens, vitamins, oligo-elements, anti-wrinkle or anti-ageing agents, botanical extracts, slimming agents, anti-radical agents, anti hair-loss agents, anti-dandruff agents, cleansing surfactants, skin-conditioning polymers, emollients and pharmaceutical active ingredients, anti-bacterial agents, anti-inflammatory agents, myorelaxants, antibiotics, antiviral agents, analgesics, anti-histamines, antipruritic agents, antipyretic agents, anesthetic agents, diagnostic agents, hormones, skin growth enhancers, pigment modulators, antiproliferative agents, antipsoriatic agents, retinoids, anti-acne medicines, antineoplastic agents, phototherapeutic agents, keratolytic agents, and analogs thereof.

26. The method according to claim 1, wherein the composition comprises at least one additive chosen from chelating agents, pH neutralization and adjustment agents, opacifiers, preservatives, leveling agents, emollients, film-forming polymers, antioxidants, perfumes, reflective agents, coalescing agents, and mixtures thereof.

27. The method according to claim 1, wherein the composition is an emulsion of an oily phase in an aqueous phase or an emulsion of an aqueous phase in an oily phase.

28. The method according to claim 27, wherein the oily phase is made up of a vegetable or plant oil, a silicone oil, a fluorinated hydrocarbon oil, a hydrocarbon oil, a mineral oil, polyisobutene, isohexadecane, a caprylic/capric triglyceride, cetearyl octanoate, $C_{12}$-$C_{14}$ alkyl benzoate, or a mixture thereof.

29. The method according to claim 1, wherein the composition comprises a water-in-oil emulsifier and/or an oil-in-water-emulsifier.

30. The method according to claim 1, wherein the branched or crosslinked polymer is a water-soluble or water-swelling polymer.

* * * * *